United States Patent [19]

Darlington et al.

[11] Patent Number: 5,545,563
[45] Date of Patent: Aug. 13, 1996

[54] HUMAN C/EBP GENE AND VECTORS FOR ITS EXPRESSION

[75] Inventors: Gretchen J. Darlington; Deborah R. Wilson, both of Houston; Margaret Wilde, Missouri City, all of Tex.

[73] Assignee: Baylor College of Medicine, Houston, Tex.

[21] Appl. No.: 205,506

[22] Filed: Mar. 4, 1994

Related U.S. Application Data

[63] Continuation-in-part of Ser. No. 29,325, Mar. 4, 1993, abandoned.
[51] Int. Cl.$^6$ ............ C12N 15/11; C12N 15/12; C12N 15/85
[52] U.S. Cl. ............ 435/320.1; 536/23.5; 536/24.31
[58] Field of Search ............ 536/23.5, 24.31; 435/320.1

[56] References Cited

PUBLICATIONS

Descombes, P. et al., "LAP, A Novel Member of the C/EBP gene Family, Encodes a Liver-Enriched Transcriptional Activator Protein, " *Genes Devel.* 4:1541–1551 (1990).

Mueller, C. R. et al., "DBP, a Liver-Enriched Transcriptional Activator, Is Expressed Late in Ontogeny and Its Tissue Specificity is Determined Posttranscriptionally, " *Cell* 61:279–291 (1990).

Landschultz, W. H. et al., "Isolation of a Recombinant Copy of the Gene Encoding C/EBP," *Genes Dev.*2:786–800 (1989).

Brunel, F. et al., "Interactions of DNA–Binding Proteins with the 5' Region of the Human Transferrin Gene," *J. Biol. Chem.* 263:10180–10185 (1988).

Metzger, S. et al., "Nuclear Factors AF–1 and C/EBP Bind to the Human ApoB Gene Promoter and Modulate its Transcriptional Activity in Hepatic Cells," *J. Biol. Chem.* 265:9978–9983 (1990).

Williams, S. C. et al., "A Family of C/EBP–Related Proteins Capable of Forming Covalently Linked Leucine Zipper Dimers In Vitro," *Genes Devel.* 5:1553–1567 (1991).

Roman, C. J. et al., "Ig/EBP– 1: A Ubiquitously Expressed Immunoglobulin Enhancer Binding Protein that is Similar to C/EBP and Heterodimerizes with C/EBP," *Genes Dev.* 4:1404–1415 (1990).

Kinoshita, S. et al., "A Member of the C/EBP Family, NF–IL6β, Forms a Heterodimer and Transcriptionally Synergizes with NF–IL6," *Proc. Natl. Acad. Sci. (U.S.A.)* 89:1473–1476 (1992).

Graves, B. et al., "Homologous Recognition of a Promoter Domain Common to the MSV LTR and the HSV tk Gene," *Cell* 44:565–576 (1986).

Johnson, P. F. et al., "Identification of a Rat Liver Nuclear Protein that Binds to the Enhancer Core Element of Three Animal Viruses, " *Genes Dev.* 1:133–146 (1987).

Christy, R. J. et al., "Differentiation–Induced Gene Expression in 3T3–L1 Preadipocytes: CCAAT/Enhancer Binding Protein Interacts with and Activates the Promoters of Two Adipocyte–Specific Genes," *Genes Dev.* 3:1323–1335 (1989).

Friedman, A. D. et al., "CCAAT/Enhancer Binding Protein Activates the Promoter of the Serum Albumin Gene in Cultured Hepatoma Cells," *Genes Dev.* 3:1314–1322 (1989).

McNight, S. L. et al., "Is CCAAT/Enhancer–Binding Protein a Central Regulator of Energy Metabolism?," *Genes Dev.* 3:2021–2024 (1989).

Birkenmeier, E. H., "Tissue–Specific Expression, Developmental Regulation, and Genetic Mapping of the Gene Encoding CCAAT/Enhancer Binding Protein," *Genes Devel.* 3:1146–1156 (1989).

Mischoulon, D. et al., "Growth–Dependent Inhibition of CCAAT Enhancer–Binding Protein (C/EBPα) Gene Expression During Hepatocyte Proliferation in the Regenerating Liver and in Culture," *Mol. Cell. Biol.* 12:2553–2560 (1992).

Umek, R. M. et al., "CCAAT–Enhancer Binding Protein: A Component of a Differntiation Switch," *Science* 251:288–292 (1991).

van Ooij, C. et al., "Temporal Expression of the Human Alcohol Dehydrogenase Gene Family During Liver Development Correlates with Differential Promoter Activation by Hepatocyte Nuclear Factor 1, CCAAT/Enhancer–Binding Protein α, Liver Activator Protein, and D–Element–Binding Protein," *Mol. Cell. Biol.* 12:3023–3031 (1992).

Christy, R. J. et al., "CCAAT/Enhancer Binding Protein Gene Promoter: Binding of Nuclear Factors During Differentiation of 3T3–L1 Preadipocytes," *Proc. Natl. Acad. Sci. (U.S.A.)* 88:2593–2597 (1991).

Friedman, A. D. et al., "Identification of Two Polypeptide Segments of CCAAT/Enhancer–Binding Protein Required for the Transcriptional Activation of the Serum Albumin Gene," *Genes Dev.* 4:1416–1426 (1990).

Herrera, R. et al., "A Direct Role for C/EBP and the AP–I–Binding Site in Gene Expression Linked to Adipocyte Differentiation," *Molec. Cell. Biol.* 9:5331–5339 (1989).

Alam, T. et al., "Differential Expression of Three C/EBP Isoforms in Multiple Tissues during the Acute Phase Response," *J. Biol. Chem.* 267:5021–5024 (1992).

*Primary Examiner*—Mindy Fleisher
*Assistant Examiner*—Philip W. Carter
*Attorney, Agent, or Firm*—Fulbright & Jaworski L.L.P.

[57] ABSTRACT

A gene sequence that encodes the human CCAAT/enhancer binding protein ("C/EBP"), and recombinant vectors that are capable of mediating the expression of the C/EBP gene are described. The gene sequence and vector can be used in methods of gene therapy to treat cancer and other diseases.

8 Claims, 7 Drawing Sheets

```
        10         20         30         40         50         60
TATAAAAGCT GGGCCGGCGC GGGCCGGGCC ATTCGCGACC CGGAGGTGCG CGGGCGCGGG
        70         80         90        100        110        120
CGAGCAGGGT CTCCGGGTGG GCGGCGGCGA CGCCCCGCGC AGGCTGGAGG CCGCCGAGGC
       130        140        150        160        170        180
TCGCCATGCC GGGAGAACTC TAACTCCCCC ATGGAGTCGG CCGACTTCTA CGAGGCGGAG
       190        200        210        220        230        240
CCGCGGCCCC CGATGAGCAG CCACCTGCAG AGCCCCCCGC ACGCGCCCAG CAGCGCCGCC
       250        260        270        280        290        300
TTCGGCTTTC CCCGGGGCGC GGGCCCCGCG CAGCCTCCCG CCCCACCTGC CGCCCCGGAG
       310        320        330        340        350        360
CCGCTGGGCG GCATCTGCGA GCACGAGACG TCCATCGACA TCAGCGCCTA CATCGACCCG
       370        380        390        400        410        420
GCCGCCTTCA ACGACGAGTT ACTGGCCGAC CTGTTCCAGC ACAGCCGGCA GCAGGAGAAG
       430        440        450        460        470        480
GCCAAGGCGG CCGTGGGCCC CACGGGCGGC GGCGGCGGCG CGACTTTGA CTACCCGGGC
       490        500        510        520        530        540
GCGCCCGCGG GCCCCGGCGG CGCCGTCATG CCCGGGGGAG CGCACGGGCC CCCGCCCGGC
       550        560        570        580        590        600
TACGGCTGCG CGGCCGCCGG CTACCTGGAC GGCAGGCTGG AGCCCCTGTA CGAGCGCGTC
       610        620        630        640        650        660
GGGGCGCCGG CGCTGCGGCC GCTGGTGATC AAGCAGGAGC CCCGCGAGGA GGATGAAGCC
       670        680        690        700        710        720
AAGCAGCTGG CGCTGGCCGG CCTCTTCCCT TACCAGCCGC CGCCGCCGCC GCCGCCCTCG
       730        740        750        760        770        780
CACCCGCACC CGCACCCGCA CCCGCCGCCC GCGCACCTGG CCGCCCGCA CCTGCAGTTC
       790        800        810        820        830        840
CAGATCGCGC ACTGCGGCCA GACCACCATG CACCTGCAGC CCGGTCACCC CACGCCGCCG
       850        860        870        880        890        900
CCCACGCCCG TGCCCAGCCC GCACCCCGCG CCCGCGCTCG GTGCCGCCGG CCTTCCGGGC
       910        920        930        940        950        960
CCTGGCAGCG CGCTCAAGGG GCTGGGCGCC GCGCACCCCG ACCTCCGCGC GAGTGGCGGC
       970        980        990       1000       1010       1020
AGCGGCGCGG GCAAGGCCAA GAAGTCGGTG GACAAGAACA GCAACGAGTA CCGGGTGCGG
      1030       1040       1050       1060       1070       1080
CGCGAGCGCA ACAACATCGC GGTGCGCAAG AGCCGCGACA AGGCCAAGCA GCGCAACGTG
      1090       1100       1110       1120       1130       1140
GAGACGCAGC AGAAGGTGCT GGAGCTGACC AGTGACAATG ACCGCCTGCG CAAGCGGGTG
      1150       1160       1170       1180       1190       1200
GAACAGCTGA GCCGCGAACT GGACACGCTG CGGGGCATCT TCCGCCAGCT GCCAGAGAGC
      1210       1220       1230       1240       1250       1260
TCCTTGGTCA AGGCCATGGG CAACTGCGCG TGAGGCGCGC GGCTGTGGGA CCGCCCTGGG
      1270       1280       1290       1300       1310
CCACCTCCGG CGGGGACCCA GGGAGTGGTT TGGGGTCGCC GGATCTCGAG GC
```

FIG.1

```
  1                             11
MET GLU SER ALA ASP PHE TYR GLU ALA GLU PRO ARG PRO PRO MET

21
SER SER HIS LEU GLN SER PRO PRO HIS ALA PRO SER SER ALA ALA 31                             41
PHE GLY PHE PRO ARG GLY ALA GLY PRO ALA GLN PRO PRO ALA PRO

51
PRO ALA ALA PRO GLU PRO LEU GLY GLY ILE CYS GLU HIS GLU THR 61                             71
SER ILE ASP ILE SER ALA TYR ILE ASP PRO ALA ALA PHE ASN ASP

81
GLU LEU LEU ALA ASP LEU PHE GLN HIS SER ARG GLN GLN GLU LYS 91                                 101
ALA LYS ALA ALA VAL GLY PRO THR GLY GLY GLY GLY GLY GLY ASP

111
PHE ASP TYR PRO GLY ALA PRO ALA GLY PRO GLY GLY ALA VAL MET 121                             131
PRO GLY GLY ALA HIS GLY PRO PRO PRO GLY TYR GLY CYS ALA ALA

141
ALA GLY TYR LEU ASP GLY ARG LEU GLU PRO LEU TYR GLU ARG VAL 151                                 161
GLY ALA PRO ALA LEU ARG PRO LEU VAL ILE LYS GLN GLU PRO ARG

171
GLU GLU ASP GLU ALA LYS GLN LEU ALA LEU ALA GLY LEU PHE PRO 181                                 191
TYR GLN PRO PRO PRO PRO PRO PRO PRO SER HIS PRO HIS PRO HIS

201
PRO HIS PRO PRO PRO ALA HIS LEU ALA ALA PRO HIS LEU GLN PHE 211                             221
GLN ILE ALA HIS CYS GLY GLN THR THR MET HIS LEU GLN PRO GLY

231
HIS PRO THR PRO PRO PRO THR PRO VAL PRO SER PRO HIS PRO ALA 241                             251
PRO ALA LEU GLY ALA ALA GLY LEU PRO GLY PRO GLY SER ALA LEU

261
LYS GLY LEU GLY ALA ALA HIS PRO ASP LEU ARG ALA SER GLY GLY 271                             281
SER GLY ALA GLY LYS ALA LYS LYS SER VAL ASP LYS ASN SER ASN

291
GLU TYR ARG VAL ARG ARG GLU ARG ASN ASN ILE ALA VAL ARG LYS 301                             311
SER ARG ASP LYS ALA LYS GLN ARG ASN VAL GLU THR GLN GLN LYS

321
VAL LEU GLU LEU THR SER ASP ASN ASP ARG LEU ARG LYS ARG VAL 331                             341
GLU GLN LEU SER ARG GLU LEU ASP THR LEU ARG GLY ILE PHE ARG

351
GLN LEU PRO GLU SER SER LEU VAL LYS ALA MET GLY ASN CYS ALA
```

FIG.2

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1312 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: C/EBP ( x i ) SEQUENCE DESCRIPTION: SEQ ID NO:1:

```
TATAAAAGCT  GGGCCGGCGC  GGGCCGGGCC  ATTCGCGACC  CGGAGGTGCG  CGGGCGCGGG      60
CGAGCAGGGT  CTCCGGGTGG  GCGGCGGCGA  CGCCCCGCGC  AGGCTGGAGG  CCGCCGAGGC     120
TCGCCATGCC  GGGAGAACTC  TAACTCCCCC  ATGGAGTCGG  CCGACTTCTA  CGAGGCGGAG     180
CCGCGGCCCC  CGATGAGCAG  CCACCTGCAG  AGCCCCCCGC  ACGCGCCCAG  CAGCGCCGCC     240
TTCGGCTTTC  CCCGGGGCGC  GGGCCCCGCG  CAGCCTCCCG  CCCCACCTGC  CGCCCCGGAG     300
```

```
CCGCTGGGCG GCATCTGCGA GCACGAGACG TCCATCGACA TCAGCGCCTA CATCGACCCG    360
GCCGCCTTCA ACGACGAGTT ACTGGCCGAC CTGTTCCAGC ACAGCCGGCA GCAGGAGAAG    420
GCCAAGGCGG CCGTGGGCCC CACGGGCGGC GGCGGCGGCG GCGACTTTGA CTACCGGGC     480
GCGCCCGCGG GCCCCGGCGG CGCCGTCATG CCCGGGGGAG CGCACGGGCC CCGCCCGGC     540
TACGGCTGCG CGGCCGCCGG CTACCTGGAC GGCAGGCTGG AGCCCCTGTA CGAGCGCGTC    600
GGGGCGCCGG CGCTGCGGCC GCTGGTGATC AAGCAGGAGC CCGCGAGGA GGATGAAGCC     660
AAGCAGCTGG CGCTGGCCGG CCTCTTCCCT TACCAGCCGC CGCCGCCGCC GCCGCCCTCG    720
CACCCGCACC CGCACCCGCA CCCGCCGCCC GCGCACCTGG CCGCCCCGCA CCTGCAGTTC    780
CAGATCGCGC ACTGCGGCCA GACCACCATG CACCTGCAGC CCGGTCACCC CACGCCGCCG    840
CCCACGCCCG TGCCCAGCCC GCACCCCGCG CCCGCGCTCG GTGCCGCCGG CCTTCCGGGC    900
CCTGGCAGCG CGCTCAAGGG GCTGGGCGCC GCGCACCCCG ACCTCCGCGC GAGTGGCGGC    960
AGCGGCGCGG GCAAGGCCAA GAAGTCGGTG GACAAGAACA GCAACGAGTA CCGGGTGCGG    1020
CGCGAGCGCA ACAACATCGC GGTGCGCAAG AGCCGCGACA AGGCCAAGCA GCGCAACGTG    1080
GAGACGCAGC AGAAGGTGCT GGAGCTGACC AGTGACAATG ACCGCCTGCG CAAGCGGGTG    1140
GAACAGCTGA GCCGCGAACT GGACACGCTG CGGGGCATCT TCCGCCAGCT GCCAGAGAGC    1200
TCCTTGGTCA AGGCCATGGG CAACTGCGCG TGAGGCGCGC GGCTGTGGGA CCGCCCTGGG    1260
CCACCTCCGG CGGGGACCCA GGGAGTGGTT TGGGGTCGCC GGATCTCGAG GC            1312
```

(2) INFORMATION FOR SEQ ID NO:2:

(i) SEQUENCE CHARACTERISTICS:
        (A) LENGTH: 360 amino acids
        (B) TYPE: amino acid
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:2:

```
Met Glu Ser Ala Asp Phe Tyr Glu Ala Glu Pro Arg Pro Pro Met Ser
 1               5                  10                  15

Ser His Leu Gln Ser Pro His Ala Pro Ser Ser Ala Ala Phe Gly
            20                  25                  30

Phe Pro Arg Gly Ala Gly Pro Ala Gln Pro Pro Ala Pro Pro Ala Ala
            35                  40                  45

Pro Glu Pro Leu Gly Gly Ile Cys Glu His Glu Thr Ser Ile Asp Ile
        50                  55                  60

Ser Ala Tyr Ile Asp Pro Ala Ala Phe Asn Asp Glu Leu Leu Ala Asp
65                  70                  75                  80

Leu Phe Gln His Ser Arg Gln Gln Glu Lys Ala Lys Ala Ala Val Gly
                85                  90                  95

Pro Thr Gly Gly Gly Gly Gly Gly Asp Phe Asp Tyr Pro Gly Ala Pro
            100                 105                 110

Ala Gly Pro Gly Gly Ala Val Met Pro Gly Gly Ala His Gly Pro Pro
            115                 120                 125

Pro Gly Tyr Gly Cys Ala Ala Ala Gly Tyr Leu Asp Gly Arg Leu Glu
        130                 135                 140
```

```
Pro  Leu  Tyr  Glu  Arg  Val  Gly  Ala  Pro  Ala  Leu  Arg  Pro  Leu  Val  Ile
145                      150                      155                      160

Lys  Gln  Glu  Pro  Arg  Glu  Glu  Asp  Glu  Ala  Lys  Gln  Leu  Ala  Leu  Ala
                    165                      170                      175

Gly  Leu  Phe  Pro  Tyr  Gln  Pro  Pro  Pro  Pro  Pro  Pro  Pro  Ser  His  Pro
               180                      185                      190

His  Pro  His  Pro  His  Pro  Pro  Ala  His  Leu  Ala  Ala  Pro  His  Leu
          195                      200                 205

Gln  Phe  Gln  Ile  Ala  His  Cys  Gly  Gln  Thr  Thr  Met  His  Leu  Gln  Pro
     210                      215                      220

Gly  His  Pro  Thr  Pro  Pro  Pro  Thr  Pro  Val  Pro  Ser  Pro  His  Pro  Ala
225                      230                      235                      240

Pro  Ala  Leu  Gly  Ala  Ala  Gly  Leu  Pro  Gly  Pro  Gly  Ser  Ala  Leu  Lys
                    245                      250                      255

Gly  Leu  Gly  Ala  Ala  His  Pro  Asp  Leu  Arg  Ala  Ser  Gly  Gly  Ser  Gly
               260                      265                 270

Ala  Gly  Lys  Ala  Lys  Lys  Ser  Val  Asp  Lys  Asn  Ser  Asn  Glu  Tyr  Arg
          275                      280                 285

Val  Arg  Arg  Glu  Arg  Asn  Asn  Ile  Ala  Val  Arg  Lys  Ser  Arg  Asp  Lys
     290                      295                 300

Ala  Lys  Gln  Arg  Asn  Val  Glu  Thr  Gln  Gln  Lys  Val  Leu  Glu  Leu  Thr
305                      310                      315                      320

Ser  Asp  Asn  Asp  Arg  Leu  Arg  Lys  Arg  Val  Glu  Gln  Leu  Ser  Arg  Glu
                    325                      330                      335

Leu  Asp  Thr  Leu  Arg  Gly  Ile  Phe  Arg  Gln  Leu  Pro  Glu  Ser  Ser  Leu
               340                      345                      350

Val  Lys  Ala  Met  Gly  Asn  Cys  Ala
          355                      360
```

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:3:

```
CGGAATTCCG                                                                    10
```

HUMAN C/EBP GENE AND VECTORS FOR ITS EXPRESSION

FIELD OF THE INVENTION

The invention relates to a gene sequence that encodes the human CCAAT/enhancer binding protein ("C/EBP"), and to recombinant vectors that are capable of mediating the expression of the C/EBP gene. The invention further pertains to methods of gene therapy that comprise the administration of such vectors to a human or animal. This invention was supported by Government funds (NIH Grant GM 32111-09). The Government has certain rights in this invention.

CROSS-REFERENCE TO RELATED APPLICATIONS:

This application is a continuation-in-part of U.S. patent application Ser. No. 08/029,325 (filed Mar. 4, 1993) now abandoned.

BACKGROUND OF THE INVENTION

I. Enhancer Sequences and Enhancer Binding PROTEINS

The development of higher eukaryotes is characterized by the differential, and tissue-specific, expression of certain genes. Among the factors that control such tissue-specific expression are diffusible positive transcriptional factors that are themselves produced in a tissue-specific manner. Certain of these transcriptional factors increase gene transcription by binding to specific DNA sequences known as "enhancer sequences" or enhancers" (Descombes, P. et al., *Genes Devel.* 4:1541–1551 (1990); see also Ptashne, M, *Nature* 335:683–689 (1988)).

Enhancer sequences are thus transcriptional regulatory sequences found in the DNA of animals and animal viruses (Khoury, G. et al., *Cell* 33:313–314 (1983); Schaffner, W. et al., *Trends Genet.* 1:224–230 (1985)). Enhancers are similar to promoters in that they act in cis, to regulate the transcription of gene sequences that are located on the same DNA molecule. They differ from promoter sequences in that their function does not depend on the position of the enhancer relative to the gene whose transcription is being enhanced. Enhancers can mediate transcription in either direction, and over considerable distances (up to several thousand base pairs).

The transcriptional factors that bind to enhancer sequences are termed "enhancer binding proteins" ("EBPs"). The ability of an enhancer to mediate gene expression in a particular cell is dependent upon the expression of an appropriate EBP in that cell. Thus, each enhancer is capable of mediating transcriptional enhancement either preferentially or exclusively in only those tissue types that express an EBP capable of binding to it.

CCAAT/enhancer binding proteins ("C/EBP") comprise a class of EBPs whose members are capable of preferentially recognizing and binding a CCAAT sequence motif (such as is found in the transferrin and ApoB genes), an enhancer core sequence motif, or the enhancer regions of several viral promoters (Landschultz, W. H. et al., *Genes Dev.* 2:786–800 (1989); Brunel, F. et al., *J. Biol. Chem.* 263:10180–10185 (1988); Metzger, S. et al., *J. Biol. Chem.* 265:9978–9983 (1990)).

The significance of human C/EBP has been elucidated by investigations of the rat and murine C/EBP analogs. The rat analog of C/EBP was initially isolated as a heat-stable protein from hepatic cells (Graves, B. et al., *Cell* 44:565–576 (1986); Johnson, P. F. et al., *Genes Dev.* 1:133–146 (1987)). High levels of expression of C/EBP were subsequently found to be limited to terminally differentiated cell types, such as adipocytes and hepatocytes, that play a central role in energy metabolism, particularly in the synthesis and mobilization of glycogen and fat (Christy, R. J. et al., *Genes Dev.* 3:1323–1335 (1989), Friedman, A. D. et al., *Genes Dev.* 3:1314–1322 (1989), McNight, S. L. et al., *Genes Dev.* 3:2021–2024 (1989)). In the adult mouse, for example, C/EBP is most abundant in the parenchymal cells of the liver and in adipose tissue. It has accordingly been proposed that C/EBP may modulate the transcription of genes that are expressed in tissues where synthesis or metabolism of lipids is an important part of their physiology (Birkenmeier, E. H. *Genes Devel.* 3:1146–1156 (1989)).

cDNA molecules encoding the rat and mouse analogs of C/EBP have been cloned (Landschultz, *Genes Devel.* 2:786–800 (1988); Xanthopoulos, K. G. et al., *Proc. Natl. Acad. Sci. (U.S.A.)* 86:4117–4121 (1989)), and expressed in tissue culture cells (Friedman, A. D. et al., *Genes Devel.* 3:1314–1322 (1989)). The predicted protein structures of the C/EBP analogs of the two species exhibit substantial homology. The C/EBP is present in single copy in the mouse genome, and is free of intervening sequences (Birkenmeier, E. H. *Genes Devel.* 3:1146–1156 (1989)).

The rat C/EBP analog is 42 kD, and is composed of 359 amino acids (Johnson, P. F. et al., *Genes Dev.* 1:133–146 (1987); Landschultz, W. H. et al., *Genes Devel.* 2:786–800 (1988)). The DNA binding domain is localized within the carboxy-terminal 80 residues (Friedman, A. D. et al., *Genes Devel.* 3:1314–1322 (1989)).

As indicated, C/EBPs comprise a family of related molecules that include, in addition to the C/EBP characterized by Landschultz, W. H. et al. (*Genes Devel.* 2:786–800 (1988)), "D-Binding Protein" (DBP) (Mueller C. R. et al., *Cell* 61:279–291 (1990)), and the "liver-enriched transcriptional activator protein ("LAP") (Descombes, P. et al., *Genes Devel.* 4:1541–1551 (1990). Additional members of the C/EBP family—designated CRP1, CRP2, and CRP3—were isolated by screening mouse and rat genomic libraries with DNA encoding a binding domain of C/EBP (Williams, S. C. et al., *Genes Devel.* 5:1553–1567 (1991).

Although significant progress has been made in identifying members of the C/EBP family, the use of these molecules, or the gene sequences that encode them, in the treatment of disease has not been reported. It would be desirable to identify therapeutic uses for these molecules and to develop means for targeting C/EBP molecules to cells and tissue in need of such therapies. The present invention provides such uses and targeting means.

SUMMARY OF THE INVENTION

The invention provides a gene sequence that encodes the human CCAAT/enhancer binding protein ("C/EBP"). It additionally provides recombinant vectors that are capable of mediating the expression of the C/EBP gene, especially under the control of tumor specific promoters. The invention further pertains to methods of gene therapy that comprise the administration of such vectors to a human or animal, and to their use in treating cancer and other diseases.

In detail, the invention provides a DNA molecule (especially a vector) that encodes a human CCAAT/Enhancer Binding Protein, and especially C/EBPα, substantially free of natural contaminants.

The invention also provides vectors that are capable of being expressed and/or propagated in a mammalian cell (especially a hepatic cell). The invention also concerns C/EBPα-encoding vectors that are capable of expressing C/EBPα.

The invention also concerns a nucleic acid molecule, especially a detectably labeled nucleic acid molecule, that is complementary to a DNA molecule encoding a human CCAAT/Enhancer Binding Protein, and especially C/EBPα, substantially free of natural contaminants.

The invention additionally concerns a human CCAAT/Enhancer Binding Protein, and especially C/EBPα, substantially free of natural contaminants.

The invention also provides a method of inhibiting the proliferation of a tumor cell (especially a hepatic tumor cell) which comprises providing to the cell a vector capable of expressing C/EBPα, and permitting the vector to express the C/EBPα.

The invention also provides a method of inducing the proliferation of a hepatic cell which comprises providing to the cell a vector capable of expressing an antagonist of C/EBPα, and permitting the vector to express the antagonist.

It, in particular, concerns a C/EBPα antagonist that is a C/EBPα antisense transcript.

The invention also provides a method of diagnosing the presence of a hepatoma cell in a tissue sample that comprises:

incubating the tissue sample, or an extract thereof, in the presence of a detectably labeled C/EBPα antisense molecule under conditions sufficient to permit the molecule to hybridize to C/EBPα mRNA present in the sample; and determining whether mRNA of the sample, or extract thereof, is capable of binding the molecule.

The invention also provides a method for determining the carcinogenic potential of a chemical which comprises:

(A) providing said chemical to a transgenic mouse having cells that each contain a mutation in at least chromosomal allele that encodes C/EBPα alleles, or to a cell line derived from said transgenic mouse; and (B) determining whether the chemical is tumorigenic to the mouse, or adversely affects the cells of the cell line.

The invention also provides a method for treating a disease characterized by a hyperproliferation of cells which comprises providing to the cells a vector capable of expressing C/EBPα, and permitting the vector to express the C/EBPα.

The invention further provides a murine cell that has a mutation in at least one chromosomal allele of the C/EBPα gene.

The invention also includes a chimeric mouse having cells that have a mutation in at least one of the mouse's chromosomal C/EBPα alleles.

The invention further provides a transgenic mouse, the mouse having cells that each contain a mutation in at least chromosomal allele that encodes C/EBPα.

BRIEF DESCRIPTION OF THE FIGURES

FIG. 1 provides the nucleotide sequence of the human C/EBPα gene (SEQ ID NO:1).

FIG. 2 provides the amino acid sequence of the C/EBPα protein (SEQ ID NO:2).

FIG. 5A shows results obtained using Hep3B2 cells; FIG. 5B shows results obtained using SAOS-2 cells. In FIGS. 5A and 5B, for each vector, the number of colonies in a category is shown as a percentage of the total number of colonies recorded. Data is presented as the mean ± standard deviations of three separate experiments.

Figure 3:
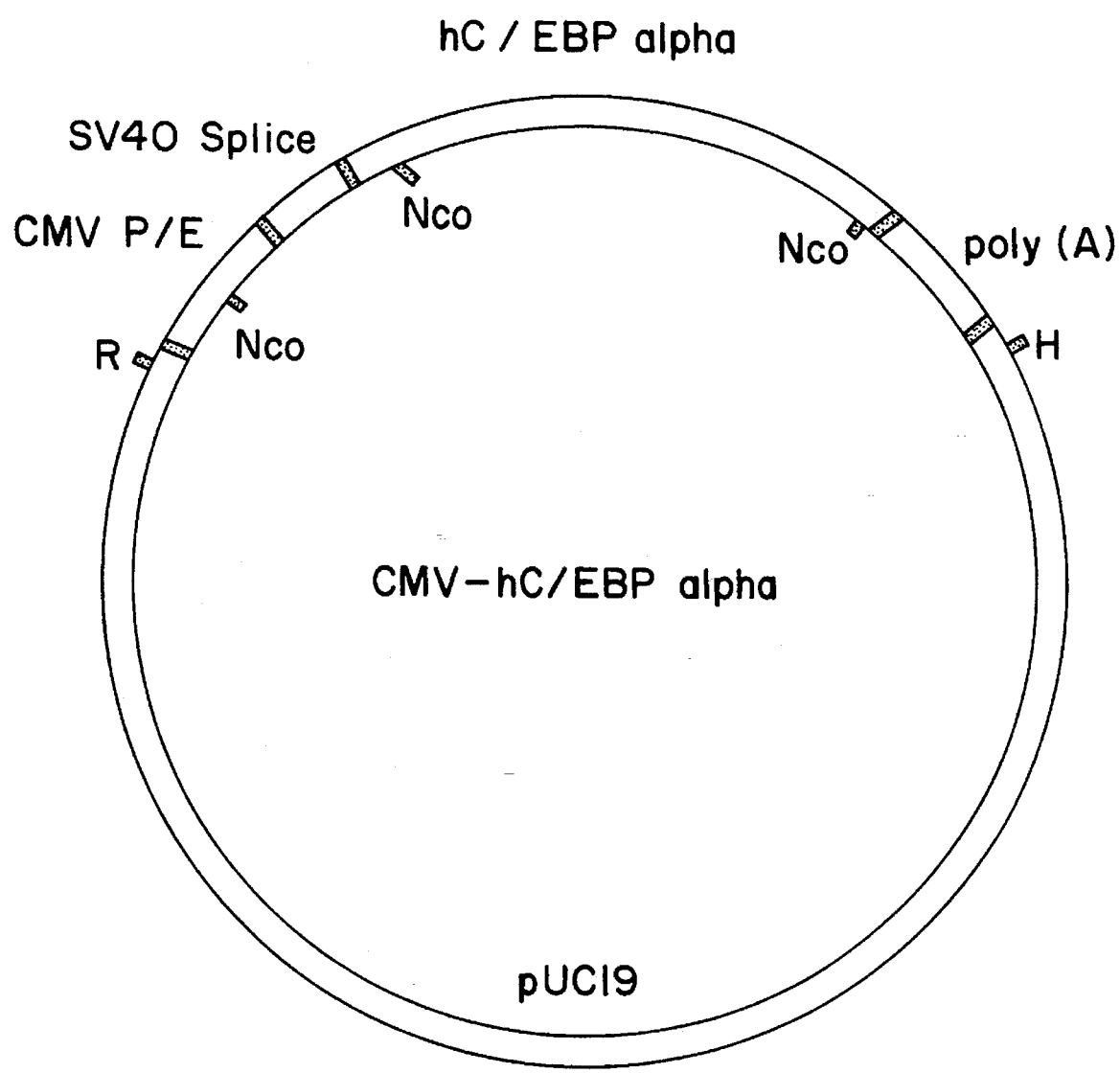
FIG. 3 provides a schematic depiction of the C/EBPα plasmid, pCMVhC/EBPα.

DESCRIPTION OF THE PREFERRED EMBODIMENTS:

I. C/EBP and THE ACUTE PHASE RESPONSE

The acute phase response represents an orchestrated response against an array of threatening or stressing conditions: bacterial and viral infection, inflammation, trauma associated with wounds, burns or surgery, and neoplasia. In addition to a localized response (at the site of trauma or injury), the acute phase response has a systemic component that includes endocrine, metabolic and neurological changes. The systemic component includes the increased synthesis and secretion of steroids and peptide hormones (eg., cytokines) that induce the expression of serum proteins (the "acute phase reactants") (Kushner, I. *Ann. N.Y. Acad Sci.* 389:39–48 (1982); Koj, A., In: "The Acute-Phase Response to Injury and Infection," (Gordon, A. H. et al., Eds.) Elsevier Science Publishers, Amsterdam (1985); Fey, G. H. et al., *Mol. Biol. & Med.* 4:323–338 (1987); Fey, G. H. et al., In: "Progress in Liver Disease," (Popper, H. et al., Eds.) W. B. Saunders & Co., Philadelphia (1990); Alam, T. et al., *J. Biol. Chem.* 267:5021–5024 (1992)).

Although multiple tissues (brain, kidney, placenta, etc.) are involved in the synthesis of the acute phase reactants, the primary site for the synthesis of these reactants is the liver (Schreiber, G., *The Plasma Proteins* 5:293–363 (1987); Thomas, T. et al., *J. Biol. Chem.* 264:5784–5790 (1989)). The stimulation of the liver in the acute phase response is mediated by the release of cytokines, and principally by interleukin-6, produced by monocytes, macrophages, T-cells, mast cells, keratinocytes, fibroblasts, as well as a variety of tumor types (Koj, A., In: "The Acute-Phase Response to Injury and Infection," (Gordon, A. H. et al., Eds.) Elsevier Science Publishers, Amsterdam (1985); Fey, G. H. et al., *Mol. Biol. & Med.* 4:323–338 (1987); Darlington, G. J. et al., *J. Cell. Biol.* 103:787–793 (1986)).

Recent studies have revealed that the role of the cytokines in regulating the acute phase reactant genes is based on their ability to regulate the activity of trans-activating factors, and, in particular, C/EBP. At least four different isoforms of C/EBP—C/EBPα, C/EBPβ, C/EBPγ and C/EBPδ—have been identified. These isoforms have been found to cross-dimerize, and to bind DNA with similar specificity (Akira, S. et al., *EMBO J.* 9:1897–1906 (1990); Poli, V. et al., *Cell* 63:643–653 (1990); Descombes, P. et al., *Genes Devel.* 4:1541–1551 (1990); Cao, Z. et al., *Genes Devel.* 5:1538–1552 (1991)). In the mouse, C/EBPα, C/EBPβ and C/EBPγ are encoded by separate genes, located on different chromosomes (Cao, Z. et al., *Genes Devel.* 5:1538–1552 (1991)).

The expression of the C/EBPα isoform has been studied in the rat. The isoform is expressed predominantly in the liver (McKnight, S. L. et al., *Genes Devel* 3:2021–2024 (1989)). In the non-growing, actively metabolizing liver, C/EBPα is highly expressed (Birkenmeier, E. H. *Genes Devel.* 3:1146–1156 (1989)). Conversely, in hepatoma cells C/EBPα expression is reduced (Friedman, A. D. et al., *Genes Dev.* 3:1314–1322 (1989)). These findings have suggested that C/EBPα expression is a growth suppressor, whose expression is inversely related to the proliferative state of the cell (Mischoulon, D. et al. *Mol. Cell. Biol.* 12:2553–2560 (1992), and that C/EBPα maintains the highly differentiated state of specialized cells by regulating their growth, and their capacity to express tissue-specific genes (Umek, R. M. et al., *Science* 251:288–292 (1991)).

The present invention derives in part from the cloning of DNA sequences that include and encode the human C/EBPα isoform (FIG. 1; SEQ ID NO:1). The isoform-encoding sequence may, in light of the present invention be isolated using any of a variety of methods.

Since the human C/EBPα gene lacks intervening sequences, it is possible to express genomic C/EBPα-encoding DNA in prokaryotes. Thus, it is not necessary to employ C/EBPα-expressing cells, and to form C/EBPα cDNA. A human DNA library may thus be obtained from any human cell. Most preferably, the cellular source will, however, be a hepatoma, or other cell, that actively expresses the C/EBPα isoform. The DNA molecules may be cloned into any suitable prokaryotic or eukaryotic vector and the vectors then screened using a probe whose sequence is the same as, or complementary to, that of SEQ ID NO:1. Suitable vectors, as well as the methods for performing such hybridization screenings are disclosed, for example, by Sambrook, J. et al., In: *Molecular Cloning A Laboratory Manual*, 2nd Edition, (Cold Spring Harbor Laboratory Press, Cold Spring Harbor, N.Y. (1989), herein incorporated by reference).

As will be appreciated, it is not necessary to employ a probe that is of the same size as that of the complete C/EBPα-encoding sequence. The probe need be only of sufficient length (15 or more nucleotides) to be capable of stabling hybridizing to DNA under reaction conditions. Examples of reaction conditions that permit the use of oligonucleotide probes are described by Haymes, B. D., et al. (In: *Nucleic Acid Hybridization, A Practical Approach*, IRL Press, Washington, D.C. (1985)) or Szostak, J. W. et al. (*Met Enzymol* 68:419–428 (1979)). Further methods for performing such hybridization assays are disclosed by Dattagupta et al. (U.S. Pat. No. 4,737,454) and by Pollard-Knight, D. (*Technique* 2:113–132 (1990)), which references are herein incorporated by reference).

Similarly, it is not necessary to employ a probe having the exact sequence of all or part of the sequence disclosed in SEQ ID NO:1. Probes whose sequence departs from the disclosed sequences may be employed provided that the sequence departures are not so substantial as to preclude the ability of the probe to hybridize to a DNA molecule having the sequence of SEQ ID NO:1, or its complement.

Alternatively, amplification procedures, such as PCR (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)) can be used to facilitate the isolation of the C/EBPα-encoding DNA. PCR methods are reviewed by Love, S. et al. (*Neuropath. Appl. Neurobiol.* 18:95–111 (1992)).

In yet another alternative, synthetic chemical methods may be used to synthesize the molecule. Thus, for example, the well-known phosphodiester or phosphotriester methods may be used.

II. THE C/EBP GENES and THE SUPPRESSION OF TUMORS

One aspect of the present invention concerns the recognition that the C/EBP genes, and in particular, the C/EBPα gene is a tumor suppressor gene.

One mechanism through which cancer may arise is through a cell's exposure to a carcinogenic agent, either chemical or radiant energy (such as UV light, x-rays, etc.). Such exposure may damage the DNA sequence of critical genes present in the genome of a cell of an animal. If this damage leads to either an impairment in the expression of the gene, or in the production of a mutant gene product, the cell may then proceed to proliferate, and ultimately result in the formation of a tumor.

One class of such critical genes has been referred to as "oncogenes" (Green, M. R., *Cell* 56:1–3 (1989)). Oncogenes are genes which are naturally in an "inactivated" state, but which, through the effect of the DNA damage are converted to an "activated" state capable of inducing tumorigenesis (i.e. tumor formation). Oncogenes have been identified in 15–20% of human tumors.

The creation of a mutant oncogene is only one of the requirements needed for tumor formation; tumorigenesis appears to also require the additional inactivation of a second class of critical genes: the "anti-oncogenes" or "tumor-suppressing genes." In their natural state these genes act to suppress cell proliferation. Damage to such genes leads to a loss of this suppression, and thereby results in tumorigenesis (Klein, G., *Science* 238:1539–1545 (1987); Weinberg, R. A., *Scientific Amer.*, Sept. 1988, pp 44–51).

The p53 gene (Green, M. R., *Cell* 56:1–3 (1989); Mowat et al., *Nature* 314:633–636 (1985); Lane, P. D. et al., *Genes Devel.* 4:1–8 (1990)) is an example of a well-characterized tumor suppressor gene. Inactivation of the p53 gene has been implicated as having a role in a wide variety of cancers including breast and lung cancers (Mackay, J. et al., *Lancet* ii:1384 (1988); James, C. D. et al., *Canc. Res.* 48:5546 (1988); Yakota, J. et al., *Proc. Nat'l. Acad. Sci. (U.S.A.)* 84:9252 (1987); Toguchida et al., *Canc. Res.* 48:3939 (1988)) and colorectal cancers (Baker, S. J. et al., *Science* 244:217–221 (1989) all herein incorporated by reference)).

The rb gene is a second well characterized tumor suppressor gene (Weinberg, R. A., *Scientific Amer.*, Sept. 1988, pp 44–51); Hansen M. F. et al,, *Trends Genet.* 4:125–128 (1988); Lee, W. -H. et al., "Molecular Biology of the Human Retinoblastoma Gene" In: *Tumor Suppressor Genes,* Klein, G. (ed.), Marcel Dekker, Inc., pp 169–200 (1990);. Individuals born with a lesion in one of the RB alleles are predisposed to early childhood development of retinoblastomas (Vogel, F., *Human Genetics* 52:1–54 (1979)). Inactivation or mutation of the second RB allele in one of the somatic cells of these susceptible individuals appears to be the molecular event that leads to tumor formation (Cavenee, W. K. et al., *Nature* 305:779–784 (1983)). Rb mutations have been found in a large number of human tumors, such as osteosarcoma (see Lee, E. Y. -H., "Diverse Mutations Lead to Inactivation of the Retinoblastoma Gene," In: *The Molecular Biology of the Retina: Basic and Clinically Relevant Studies,* Wiley-Liss, Inc., pp. 221–240 (1991), herein incorporated by reference).

The level of C/EBPα expression is inversely related to the tumorigenic potential of a cell. Such a relationship supports the possibility that the C/EBPα gene is a tumor suppressor.

III. MAMMALIAN VECTORS

In one embodiment, the present invention permits the expression (i.e. transcription and translation) of the C/EBPα-encoding sequences. This is accomplished, in part, through the isolation and identification of the C/EBPα-encoding sequences, in a form that is "substantially free of natural contaminants." As used herein, a molecule is said to be "substantially free of natural contaminants" if it has been produced recombinantly, or synthetically, or if it has been purified from any material with which it is typically found in its natural environment.

Such sequences are preferably incorporated into "vector" molecules. The term "vector," as used herein is intended to denote any viral or plasmid molecule that is capable of being introduced (as by transformation, electroporation, transfection, etc.) and/or propagated (i.e. replicated) in a prokaryotic or eukaryotic cell.

For some purposes, such as the isolation of C/EBPα in quantities sufficient to permit the isolation of antibodies, or to facilitate in vitro mutagenesis or characterization, it may be desirable to express C/EBPα in prokaryotic hosts, especially bacteria using prokaryotic vectors. Preferred prokaryotic vectors include plasmids such as those capable of replication in *E. coli* such as, for example, pBR322, ColE1, pSC101, pACYC 184, πVX. Such plasmids are, for example, disclosed by Sambrook, J. et al. (In: *Molecular Cloning, A Laboratory Manual*, 2nd Ed., Cold Spring Harbor Press, Cold Spring Harbor, N.Y. (1989)). Bacillus plasmids include pC194, pC221, pT127, etc. Such plasmids are disclosed by Gryczan, T. (In: *The Molecular Biology of the Bacilli*, Academic Press, NY (1982), pp. 307–329). Suitable Streptomyces plasmids include pIJ101 (Kendall, K. J., et al., *J. Bacteriol.* 169:4177–4183 (1987)), and Streptomyces bacteriophages such as øC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

If desired, yeast and fungal vectors may be used. Examples of suitable yeast vectors include the yeast 2-micron circle, the expression plasmids YEP13, YCP and YRP, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982)).

Most preferably, the C/EBPα-encoding sequences will be expressed in mammalian cells, using eukaryotic vectors (especially, a eukaryotic viral or retroviral vector). Typically, such vectors will be designed to include a prokaryotic replicon, and selectable marker, such that the propagation of the vector in bacterial cells can be readily accomplished. In order to replicate in mammalian cells, however, the vectors will also contain a viral replicon, such as the replicon of Epstein-Barr virus, bovine papilloma virus, parvovirus, adenovirus, or papovirus (i.e. SV40 or polyoma virus).

Plasmid vectors using papovirus replicons ultimately kill their host cells, and are thus preferred for transient expression studies. SV40-based vectors that may be used include pMSG (Pharmacia), pSVT7, pMT2 (Kaufman, R. J., In: *Genetic Engineering: Principles and Methods Vol. 9* (Setlow, J. K., Ed.) Plenum Publishing, NY (1987)).

In contrast, vectors that employ the replicons of Epstein-Barr, or bovine papilloma viruses do not generally cause cell death, and are thus suitable for long term propagation. Examples of such vectors include BPV-1, pBV-1MTHA, pHEBo, p205 (Shimuzu, Y. et al., *Mol. Cell. Biol.* 6:1074 (1986); Kioussis, D. et al. *EMBO J.* 6:355 (1987); Sambrook, J. et al., *EMBO J.* 4:91 (1985).

Sambrook, J. et al., herein incorporated by reference, provide a review of the characteristics of mammalian vectors (In: *Molecular Cloning, A Laboratory Manual*, 2nd Ed., Cold Spring Harbor Press, Cold Spring Harbor, N.Y. (1989).

The most preferred vector is a derivative of pUC19 which has been modified to contain a CMV promoter/enhancer site. The CMV promoter is operably linked to and therefore directs the transcription of the C/EBPα-encoding sequence. The vector additionally contains a 3' poly adenylation site. The C/EBPα may be expressed directly, or as a fusion with another protein. Most preferably, it will be expressed directly.

Any suitable mammalian promoter may be employed to mediate expression, however, it is preferable to employ tumor-specific promoters (i.e. promoters that are more active in tumor cells than in non-tumor cells). Preferred examples of such a promoters include, the α-fetoprotein promoter, the amylase promoter (especially, the murine amylase promoter), the cathepsin E promoter, the M1 muscarinic receptor promoter, the γ-glutamyl transferase promoter, etc., and especially, the CMV promoter.

Suitable CMV promoter sequences can be obtained from the CMV-promoted β-galactosidase expression vector, CMBβ (MacGregor, G. R. et al., *Nucleic Acids Res.* 17:2365 (1989)). Suitable α-fetoprotein promoter sequences are present in the vectors PSVA F0.4 CAT$^A$ and PAF 5.1 (δ2-CAT) (Watanabe et al., *J. Biol. Chem.* 262:4812–4818 (1987)). The PSVA F0.4 CAT$^A$ vector contains 5 kb of flanking DNA with a deletion of approximately 2 kb between −1.0 and −3.0. The PAF 5.1 (δ2-CAT) vector encompasses approximately 400 base pairs of the α-fetoprotein 5' flanking sequence which lies between −3.7 kb and −3.3 kb, coupled to the SV40 promoter in the PSC1 CAT vector. Suitable amylase promoter, especially murine amylase promoter sequences are described by Wu et al. (*Molec. Cell. Biol.* 11:4423–4430 (1991)). Suitable cathepsin E promoter sequences are described by Azuma et al. (*J. Biol. Chem.* 267:1609–1614 (1992)). Suitable M1 muscarinic receptor promoter sequences are described by Fraser et al. (*Molec. Pharmacol.* 36:840–847 (1989)) and by Bonner (*Trends Neurosci.* 12:148–151 (1989)). Vectors containing suitable γ-glutamyl transferase promoter sequences are described by Rajagopalan, S. et al., *J. Biol. Chem.* 265:11721–11725 (1990).

IV. USES OF THE INVENTION

Production of Transgenic Animals Having Altered Chromosomal Alleles of C/EBP Genes The present invention also provides transgenic animals, especially transgenic mice, that possess predetermined mutations and alleles in their chromosomal C/EBP genes. Such animals can be used to study the physiologic significance of the C/EBP gene. The animals can also be used to identify agents that are capable of mimicking, inhibiting, or stimulating C/EBP gene expression.

The production of chimeric or transgenic animals having a predetermined mutation in the sequence of at least one of the two alleles of a C/EBP gene can be accomplished through the use of either replacement or insertion vectors. The use of insertion vectors results in the introduction of vector sequences into the chromosome of the recipient; the use of replacement vectors results in the exchange of a host sequence for that carried by the vector. Replacement vectors may be used to accomplish the deletion of a gene sequence.

Either vector is capable of mutating either a single allele, or both alleles, of the cellular genes that C/EBP molecules; it is possible to readily identify such dual mutational events (for example through the use of PCR (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; and Saiki, R. et al., U.S. Pat. No. 4,683,194)), or other methods). Since the frequency of such dual mutational events is the square of the frequency of a single mutational event, cells having mutations in both chromosomal C/EBP alleles will be only a very small proportion of the total population of mutated cells. Thus, the use of classical interbreeding may be preferred in order to obtain homozygous animals.

Most preferably, replacement vectors are used to produce the cells and the chimeric or transgenic animals of the present invention. Replacement (or insertion) vectors are preferably DNA molecule(s) which may be single stranded, but are preferably double stranded. The DNA molecule(s) may be introduced to the cell as one or more RNA molecules which may be converted to DNA by reverse transcriptase or by other means. Preferably, the DNA molecule will be double-stranded linear molecule. In the best mode for conducting this embodiment of the invention, such a molecule is obtained by cleaving a closed covalent circular molecule to form a linear molecule. Such vectors will preferably contain a selectable marker gene sequence flanked on at least one side, and preferably on both sides, by a region having homology with the desired C/EBP allele that is to be altered. A consequence of the use of such a vector is the replacement of the chromosomal allele with the sequence of the selectable marker gene.

Most preferably, the vector molecule(s) which are to be introduced into the recipient cell contains a region of homology with a region of the gene that encodes the C/EBP gene that is to be mutated. In a preferred embodiment, the DNA molecule will contain two regions of homology with the cell's C/EBP allele. These regions of homology will preferably flank the precise sequence whose incorporation into the chromosomal allele is desired.

Most preferably, the replacement vector will also contain flanking gene sequences capable of "negative selection" as well as "positive selection," such as the tk gene that encodes thymidine kinase, or the hprt gene that encodes hypoxanthine phosphoribosyl transferase. Cells expressing active thymidine kinase are able to grow in media containing HATG, but are unable to grow in media containing nucleoside analogs such as 5-azacytidine (Giphart-Gassler, M. et al., *Mutat. Res.* 214:223–232 (1989)). Cells containing an active HSV-tk gene are incapable of growing in the presence of gancyclovir or similar agents (Giphart-Gassler, M. et al., *Mutat. Res.* 214:223–232 (1989)). Cells which express an active HPRT enzyme are unable to grow in the presence of certain nucleoside analogs (such as 6-thioguanine, 8-azapurine, etc.), but are able to grow in media supplemented with HAT (hypoxanthine, aminopterin, and thymidine). Conversely, cells which fail to express an active HPRT enzyme are unable to grow in media containing HATG, but are resistant to analogs such as 6-thioguanine, etc. (Littlefield, J. W., *Science* 145:709–710 (1964)). A preferred gene for this purpose is the hprt gene.

In a preferred embodiment, the vector will also contain a selectable marker gene sequence (although, as described below, such sequence can be provided to recipient cells using a second vector or nucleic acid molecule). Examples of such detectable gene sequences include the hprt gene, the tk gene (and especially the tk gene of herpes simplex virus) herein incorporated by reference), the nptII gene (Thomas, K. R. et al., *Cell* 51:503–512 (1987); Mansour, S. L. et al., *Nature* 336:348–352 (1988), both references herein incorporated by reference), or other genes which confer resistance to amino acid or nucleoside analogs, or antibiotics, etc. The detectable marker gene may be any gene which can complement for a recognizable cellular deficiency.

The nptII gene (Southern, P. J., et al., *J. Molec. Appl. Genet.* 1:327–341 (1982); Smithies, O. et al., *Nature* 317:230–234 (1985), which references are incorporated herein by reference) is the most preferred detectable marker gene sequence. Constructs which contain either an NptII gene (or an hprt gene) and a tk gene are especially preferred.

Thus, in one method for using a replacement vector, the vector is linearized and introduced into pluripotent recipient cells (preferably embryonic stem ("ES") cells), or equivalent (Robertson, E. J., In: *Current Communications in Molecular Biology,* Capecchi, M. R. (ed.), Cold Spring Harbor Press, Cold Spring Harbor, N.Y. (1989), pp. 39–44, which reference is incorporated herein by reference). The transfected pluripotent cell may be cultured in vivo, in a manner known in the art (Evans, M. J. et al., *Nature* 292:154–156 (1981)) to form a chimeric or transgenic animal. ES cells have a normal karyotype (Evans, M. J. et al., *Nature* 292:154–156 (1981); Martin, G. R. et al., *Proc. Natl. Acad. Sci. (U.S.A.)* 78:7634–7638 (1981)).

Any ES cell may be used in accordance with the present invention. It is, however, preferred to use primary isolates of ES cells. Such isolates may be obtained directly from embryos such as the CCE cell line disclosed by Robertson, E. J., In: *Current Communications in Molecular Biology,* Capecchi, M. R. (ed.), Cold Spring Harbor Press, Cold Spring Harbor, N.Y. (1989), pp. 39–44), or from the clonal isolation of ES cells from the CCE cell line (Schwartzberg, P. A. et al., *Science* 246:799–803 (1989), which reference is incorporated herein by reference). Such clonal isolation may be accomplished according to the method of E. J. Robertson (In: *Teratocarcinomas and Embryonic Stem Cells: A Practical Approach,* (E. J. Robertson, Ed.), IRL Press, Oxford, 1987) which reference and method are incorporated herein by reference. The purpose of such clonal propagation is to obtain ES cells which have a greater efficiency for differentiating into an animal. Clonally selected ES cells are approximately 10-fold more effective in producing transgenic animals than the progenitor cell line CCE. For the purposes of the recombination methods of the present invention, clonal selection provides no advantage. An example of ES cell lines which have been clonally derived from embryos are the ES cell lines, AB1 (hprt$^+$) or AB2.1 (hprt$^-$).

The DNA molecule containing the desired gene sequence may be introduced into the pluripotent cell by any method which will permit the introduced molecule to undergo recombination at its regions of homology. Some methods, such as direct microinjection, or calcium phosphate transformation, may cause the introduced molecule to form concatemers upon integration. These concatemers may resolve themselves to form non-concatemeric integration structures. Since the presence of concatemers is not desired if the vectors contain coding sequences, methods which produce concatemers are generally not preferred. In a preferred embodiment, the DNA is introduced by electroporation (Toneguzzo, F. et al., *Nucleic Acids Res.* 16:5515–5532 (1988); Quillet, A. et al., *J. Immunol.* 141:17–20 (1988); Machy, P. et al., *Proc. Natl. Acad. Sci. (U.S.A.)* 85:8027–8031 (1988); all of which references are incorporated herein by reference).

After electroporation, the ES cells are cultured in medium that selects for transfectants that have received and integrated the selectable marker gene sequence. The culturing conditions are then altered, such that they now select against recipient cells that have acquired the negative selection gene. In a preferred embodiment of this method, such positive and negative selection is accomplished simultaneously by culturing the cells under conditions that select for the selectable marker gene, but select against the presence of the negative selection gene. Since all of these sequences are present on the same targeting vector molecule, such dual selection requires a recombinational event to occur.

The survivors of such dual selection are then screened either for the function of the chromosomal allele, or more preferably, by Southern blot analysis for clones in which the selectable marker gene sequence has replaced the originally present chromosomal allele.

After selection for cells which have incorporated the desired DNA molecule (for example by selection for G418 resistant cells when the detectable marker gene sequence is an expressible nptII gene sequence), the cells are cultured, and the presence of the introduced DNA molecule is confirmed as described above. Any of a variety of methods may be used to identify cells which have undergone the desired recombinational event. Direct screening of clones, use of PCR, use of hybridization probes, etc., may all be employed for this purpose.

ES cells that have undergone recombination may be used to produce chimeric and transgenic animals. A chimeric animal is one in which only some of the animals' cells contain the modified C/EBP gene. in contrast, a transgenic animal is an animal in which the modified C/EBP construct is present in every cell. The ES cells are preferably cultured on stromal cells (such as STO cells (especially SNC4 STO cells) and/or primary embryonic fibroblast cells) as described by E. J. Robertson (In: *Teratocarcinomas and Embryonic Stem Cells: A Practical Approach,* (E. J. Robertson, Ed.), IRL Press, Oxford, 1987, pp 71–112), which reference is incorporated herein by reference. Methods for the production and analysis of chimeric mice are disclosed by Bradley, A. (In: *Teratocarcinomas and Embryonic Stem Cells: A Practical Approach,* (E. J. Robertson, Ed.), IRL Press, Oxford, 1987, pp 113–151), which reference is incorporated herein by reference. The stromal (and/or fibroblast) cells serve to eliminate the clonal overgrowth of abnormal ES cells. Most preferably, the cells are cultured in the presence of leukocyte inhibitory factor ("lif") (Gough, N. M. et al., *Reprod. Fertil. Dev.* 1:281–288 (1989); Yamamori, Y. et al., *Science* 246:1412–1416 (1989), both of which references are incorporated herein by reference). Since the gene encoding lif has been cloned (Gough, N. M. et al., *Reprod. Fertil. Dev.* 1:281–288 (1989)), it is especially preferred to transform stromal cells with this gene, by means known in the art, and to then culture the ES cells on transformed stromal cells that secrete lif into the culture medium.

The invention thus provides a method for altering the natural sequence of an endogenous chromosomal C/EBP gene through the introduction of a "desired gene sequence" into that gene. The "desired gene sequence" may be of any length, and have any nucleotide sequence. It may comprise one or more gene sequences which encode complete proteins, fragments of such gene sequences, regulatory sequences, etc. Significantly, the desired gene sequence may differ only slightly from a native gene of the recipient cell (for example, it may contain single, or multiple base alterations, insertions or deletions relative to the native gene). The use of such desired gene sequences permits one to create subtle and precise changes in the chromosomal allele of the recipient cell. Thus, the present invention provides a means for manipulating and modulating the expression and regulation of C/EBP genes.

In particular, the invention provides a means for manipulating and modulating the expression and protein structure of genes that encode C/EBP molecules through the replacement of a naturally present gene sequence with a "non-selectable" "desired gene sequence." A gene sequence is non-selectable if its presence or expression in a recipient cell provides no survival advantage to the cell under the culturing conditions employed. Thus, by definition, one cannot select for cells which have received a "non-selectable" gene sequence in one of its genes. An example of such a sequence is one that encodes a non-functional C/EBP allele. In contrast, a "dominant" gene sequence is one which can, under certain circumstances, provide a survival advantage to a recipient cell. The neomycin resistance conferred by the nptII gene is a survival advantage to a cell cultured in the presence of neomycin or G418. The nptII gene is thus a dominant, rather than a non-selectable gene sequence.

In particular, the invention permits the replacement of the naturally present gene sequence of a recipient cell with an "analog" sequence capable of causing the expression of an "analog C/EBP molecule." As used herein an "analog C/EBP molecule" is a molecule that is capable of acting in the same or a similar manner as a naturally occurring C/EBP molecule. A sequence is said to be an "analog" of another sequence if the two sequences are substantially similar in sequence, but have minor changes in sequence corresponding to single base substitutions, deletions, or insertions with respect to one another, or if they possess "minor" multiple base alterations.

Since the C/EBPα protein exhibits the properties of a tumor suppressor, the transgenic animals of the present invention are predisposed to cancer. Such animals can therefore be used to screen and evaluate the carcinogenic potential of chemicals and other agents. Thus, the animals of the present invention provide an alternative to those described by Leder, P. et al. (U.S. Pat. No. 4,736,866) which contain cells having an exogenously added activated oncogene sequence. Although the animals of Leder, P. et al. are disclosed as being useful for assaying for carcinogenic materials, the precise location and structure of the added oncogene sequence in the animals is unknown, and cannot be experimentally controlled. Thus, the value of the animals as a model for oncogenesis is significantly impaired. The present animals complement the P53 deficient animals described by Donehower, L. A. et al. (*Nature* 356:215–221 (1992); PCT Application US92/00295) and the rb deficient animals of Bradley, A. et al. (PCT Application US/93/05584).

As discussed below, homozygous C/EBP deficient animals exhibit neonatal hypoglycemia and glycogen storage diseases. Such animals can thus be used as in vivo models for identifying agents capable of treating these disorders in humans and animals.

The cell lines derived from such transgenic mice (or from their embryonic stem cell progenitors) can be used to assay for the carcinogenic potential of chemicals and other agents. Such assays would evaluate the effect of such agents on the morphology, growth characteristics, etc. of the C/EBP deficient cells. Thus, one may incubate such cells in the presence of a suspected affector of C/EBP expression to determine whether the compound is able to affect C/EBPα expression. In particular, such assays may evaluate changes in the expression of steroids and peptide hormones (e.g., cytokines) that induce the expression of "acute phase reactants," or of the reactants themselves.

B. Use in the Diagnosis of Hepatic Function

The present invention permits a determination of the presence and extent of C/EBPα expression in hepatic or other tissue. As indicated above, the level of C/EBPα expression is inversely related to the tumorigenic potential of such cells. Such a relationship supports the possibility that C/EBPα expression affects or even prevents tumorigenicity. In one embodiment, the C/EBPα sequences of the present invention can be expressed to yield C/EBPα. This material has been used to elicit anti-C/EBPα antibodies that can be used in an immunoassay format to quantitate the level and extent of C/EBPα expression. Suitable immunoassay formats are described, for example, by Fackrell (*J. Clin. Immunoassay* 8:213–219 (1985)), Yolken, R. H. (*Rev. Infect. Dis.* 4:35 (1982)), Collins, W. P. (In: *Alternative Immunoassays*, John Wiley & Sons, NY (1985)), Ngo, T. T. et al. (In: *Enzyme Mediated Immunoassay*, Plenum Press, NY (1985)), and In: *ELISA and Other Solid Phase Immunoassays* (Kemeny, D. M. et al., Eds.), John Wiley & Sons, NY (1988)).

Hence, the present invention provides an immunoassay format that employs anti-C/EBPα antibodies to detect and/ or quantitate the level or concentration of C/EBPα in a sample. In a preferred embodiment, the immunoassay may be conducted in situ using, for example, tissue or biopsy samples, etc. Alternatively, the assay may be conducted on unpurified, partially purified or purified preparations obtained from a tissue sample.

In an alternative embodiment, the presence of C/EBPα mRNA in such samples can be detected using C/EBP-specific nucleic acid probes (either DNA or RNA) that are capable of hybridizing to the sequence of C/EBPα mRNA. Preferably, such probes will be about 10–30 nucleotides in length, most preferably, about 15–24 nucleotides in length. Such molecules will also be preferably labeled with a detectable label. In this regard, any detectable label (i.e. enzyme, isotopic, fluorescent, etc.) may be used. The presence of hepatic cells in a biopsied tissue of normal liver that fail to produce mRNA capable of binding such C/EBP-specific probes is diagnostic of the presence of hepatoma.

In a preferred method, "antisense molecules" are employed to assay C/EBPα expression. Such an assay may be performed using live tissue, either in vivo, or upon tissue culture, ex vivo.

In general, a C/EBPα "antisense molecule" is a nucleic acid (either DNA or RNA) whose sequence is complementary to the sequence of C/EBPα mRNA molecule (or its corresponding gene) such that it is capable of binding to, or hybridizing with, the mRNA molecule (or the gene), and thereby impairing (i.e. attenuating or preventing) the translation of the mRNA molecule into a gene product. Such molecules include "antisense transcripts" which are preferably 100–500 nucleotides in length, as well as "antisense oligonucleotides, which are of a length sufficient to permit sequence specific hybridization with a C/EBPα sequence. Preferably, the antisense oligonucleotide will be about 10–30 nucleotides in length, most preferably, about 15–24 nucleotides in length.

Alternatively, one may use antisense oligonucleotides that are of a length that is too short to be capable of stably hybridizing to the C/EBPα mRNA under physiologic, in vivo conditions. Such an oligonucleotide may be from about 6–10, or more nucleotides in length. To be used in accordance with the present invention, such an oligonucleotide is preferably modified to permit it to bind to a locus of the translation region of a C/EBPα-encoding mRNA. Examples of such modified molecules include oligonucleotides bound to an antibody (or antibody fragment), or other ligand (such as a divalent crosslinking agent (such as, for example, trimethylpsoralin, 8-methoxypsoralin, etc.) capable of binding to single-stranded C/EBPα mRNA molecules.

An anti-C/EBPα antisense oligonucleotide bound to one reactive group of a divalent crosslinking agent (such as psoralin (for example, trimethylpsoralin, or 8-methoxypsoralin) adduct would be capable of crosslinking to C/EBPα mRNA upon activation with 350–420 nm UV light. Thus, by regulating the intensity of such light (as by varying the wattage of the UV lamp, by increasing the distance between the cells and the lamp, etc.) one may control the extent of binding between the antisense oligonucleotide and the C/EBPα mRNA of a cell. This, in turn, permits one to control the degree of attenuation of C/EBPα gene expression in a recipient cell.

In accordance with the present invention, C/EBPα antisense transcripts of 400–500 bp have been formed and found to be capable of inhibiting C/EBPα activity. The success of such experiments indicates that smaller "antisense oligonucleotides" may alternatively be used to inhibit C/EBPα expression. Antisense oligonucleotides are disclosed in European Patent Application Publication Nos. 263,740; 335, 451; and 329,882, and in PCT Publication No. WO90/ 00624, all of which references are incorporated herein by reference.

In general, the antisense transcript or oligomer is prepared in accordance with the nucleotide sequence of the C/EBPα gene. The sequence of the antisense transcript or oligonucleotide may contain one or more insertions, substitutions, or deletions of one or more nucleotides provided that the resulting transcript or oligonucleotide is capable of binding to or hybridizing with the entire C/EBPα mRNA sequence, or any desired fragment thereof.

Any means known in the art may be used to synthesize the antisense transcripts or oligonucleotides, or the above-described probes of the present invention (Zamechik et al., *Proc. Natl. Acad. Sci.* (*U.S.A.*) 83:4143 (1986); Goodchild et al., *Proc. Natl. Acad. Sci.* (*U.S.A.*) 85:5507 (1988); Wickstrom et al., *Proc. Natl. Acad. Sci.* (*U.S.A.*) 85:1028; Holt, J. T. et al., *Mol. Cell. Biol.* 8:963 (1988); Gerwirtz, A. M. et al., *Science* 242:1303 (1988); Anfossi, G., et al., *Proc. Natl. Acad. Sci.* (*U.S.A.*) 86:3379 (1989); Becker, D., et al., *EMBO J.* 8:3679 (1989); all of which references are incorporated herein by reference). Automated nucleic acid synthesizers may be employed for this purpose. In addition, desired nucleotides of any sequence can be obtained from any commercial supplier of such custom molecules.

Most preferably, the antisense transcripts or oligonucleotides, or probes of the present invention may be prepared using solid phase "phosphoramidite synthesis." The synthesis is performed with the growing nucleotide chain attached to a solid support derivatized with the nucleotide which will be the 3'-hydroxyl end of the transcript or oligonucleotide. The method involves the cyclical synthesis of DNA using monomer units whose 5'-hydroxyl group is blocked (preferably with a 5'-DMT (dimethoxytrityl) group), and whose amino groups are blocked with either a benzoyl group (for the amino groups of cytosine and adenosine) or an isobutyryl group (to protect guanosine). Methods for producing such derivatives are well known in the art.

Alternatively, the negative strand of C/EBPα may be cloned and antisense molecules may be prepared using recombinant methods.

C. Use in the Treatment of Hepatic and Other Cancers

The present invention provides a means for treating hepatic and other cancers whose onset or maintenance is characterized by and dependent upon a decreased cellular expression of C/EBPα. In particular, the invention provides a "method of inhibiting the proliferation of a cancer cell." As used herein, the proliferation of a cancer cell is said to be "inhibited" if the rate or extent of its proliferation is diminished relative to untreated cancer cells.

The present invention accomplishes such treatment by causing such hepatic or tumor cells to increase their expression of C/EBPα. Two means for inducing such increased expression are particularly preferred.

In one embodiment, DNA encoding either a functional C/EBPα gene, variants of that gene, or other genes which influence the activity of the C/EBPα gene are introduced into vectors that are capable of transfecting tumor cells of humans or animals (particularly mammals) in order to provide a "gene therapy" for the cancer. Most preferably, viral or retroviral vectors are employed for this purpose. Examples of suitable vectors, in addition to those identified above, are discussed by Fletcher, F. A. et al. (*J. Exper. Med.* 174:837–845 (1991)), Mäkelä, T. P. et al. (*Gene* 118:293–294 (1992)), Porgador, A. et al. (*Canc. Res.* 52:3679–3686 (1992)), Yoshimura, K. et al. (*Nucl. Acids Res.* 20:3233–3240 (1992)), Lim, B. et al. (*Proc. Natl. Acad. Sci. (U.S.A.)* 86:8892–8896 (1989)), Ohi, S. et al. (*Gene* 89:279–282 1990)), and Russel, S. J. et al. (*J. Virol.* 66:2821–2828 (1992)).

In an especially preferred embodiment, the gene sequences are transcribed from promoters that are transcribed only, or at least preferentially, in tumor cells. Examples of such promoters include those that direct the transcription of tumor specific antigens such as α-fetoprotein, carcinoembryonic antigen, amylase, γ-glutamyl transferase, etc.

The principles of gene therapy are disclosed by Oldham, R. K. (In: *Principles of Biotherapy*, Raven Press, NY, 1987), and similar texts. Disclosures of the methods and uses for gene therapy are provided by Boggs, S. S. (*Int. J. Cell Clon.* 8:80–96 (1990)); Karson, E. M. (*Biol. Reprod.* 42:39–49 (1990)); Ledley, F. D., In: *Biotechnology, A Comprehensive Treatise, volume 7B, Gene Technology*, VCH Publishers, Inc. NY, pp 399–458 (1989)); all of which references are incorporated herein by reference. Such gene therapy can be provided to a recipient in order to treat (i.e. suppress, or attenuate) an existing condition, or to provide a prophylactic gene therapy to individuals who, due to inherited genetic mutations, or somatic cell mutation, contain cells having impaired gene expression (for example, only a single functional allele of the C/EBPα gene).

In an especially preferred embodiment, adenovirus vectors are employed to deliver the C/EBPα-encoding sequences to the liver (as by injecting such vectors directly into the recipient's portal vein). The nature of the blood flow to the liver makes it likely that any vector delivered via the portal vein will come to reside within the hepatocytes and tumors of the liver, but is unlikely to extend outside of that organ to other tissues. In sum, the vectors are likely to become "trapped" in the liver tissue which serves as a filter for the body.

In a second embodiment, the C/EBPα-encoding sequences are used to identify C/EBPα, a variant thereof, or a synergistic agent, which are then provided to tumor cells in order to amplify the effective concentration or activity of nascent C/EBPα As used herein, such synergistic agents include proteins or non-protein factors that facilitate the binding of C/EBPα to its target sequence, or which stabilize either C/EBPα or C/EBPα mRNA from degradation or inactivity, or which act to increase the rate of transcription or translation of the C/EBPα mRNA. Such molecules can be readily identified by screening candidate agents for their capacity to increase C/EBPα concentration, stability, or activity. Thus, for example, one may incubate normal liver cells in the presence of both an C/EBPα antisense transcript or oligonucleotide and a suspected synergistic agent. The cells would be monitored in order to determine whether the compound is able to ameliorate the inhibition of C/EBPα expression caused by the C/EBPα antisense transcript or oligonucleotide.

Conversely, one may incubate cells in the presence of a suspected antagonist compound. The cells would be monitored in order to determine whether the compound is able to derepress C/EBPα expression. Thus, the present invention includes a "screening assay" capable of identifying either antagonists of C/EBPα or synergistic agents In particular, such assays may evaluate changes in the expression of steroids and peptide hormones (eg., cytokines) that induce the expression of "acute phase reactants," or of the reactants themselves.

D. Use in the Treatment of Hepatic Disfunction or Liver Regeneration

As indicated above, the present invention permits the identification of C/EBPα antagonists (both proteinaceous, and non-proteinaceous, such as antisense transcripts or oligonucleotides) that can specifically impair the level or extent of C/EBPα expression or activity.

Such molecules are useful in treating hepatic disfunction, or in facilitation the regeneration or hypertrophy of the liver.

One manner in which a C/EBPα antisense transcript or oligonucleotide may achieve these goals is by having a sequence complementary to that of the translation initiation region of the C/EBPα mRNA and of sufficient length to be able to hybridize to the C/EBPα mRNA transcript.

The antisense transcripts, oligonucleotides and other C/EBPα antagonists of the present invention may be used to immortalize valuable cell types (such as primary liver tissue, cells, etc.) which would otherwise have a transient period of proliferative viability. They may thus be used for research or to permit or facilitate the accumulation of large numbers of cells, as for organ or tissue grafts or transplants. In one embodiment, therefore, the agents of the present invention may be used in conjunction with methods for organ or tissue culture to facilitate such methods.

A use is said to be therapeutic if it alters a physiologic condition. The agents of the present invention may be used locally or systemically for a desired therapeutic purpose. They may be used in pharmaceuticals, and the like, which may comprise, for example, an antisense transcript or oligonucleotide, or the equivalent of either, and a lipophilic carrier or adjunct, preferably dissolved in an appropriate solvent. Such a solvent may be, for example, a water-ethanol mixture (containing 10% to 30% v/v or more ethanol. Such preparations may contain 000.1% to 1.0% of the antisense molecule. Suitable carriers, adjuncts and solvents are described in Remington's Pharmaceutical Sciences (16th ed., Osol, A., Ed., Mack, Easton Pa. (1980), which reference is incorporated herein by reference).

Since the antisense molecules and other C/EBPα antagonists of the present invention are capable of stimulating hepatic cell proliferation, they may be used to promote recovery from burns, or after surgery, or to restore atrophied tissue, etc. For such an embodiment, these agents may be formulated with antibiotics, anti-fungal agents, or the like, for local or systemic administration.

E. Use in Research and Drug Development

The gene sequences and vectors of the present invention, quite apart from their therapeutic or diagnostic uses, may be used to investigate gene regulation, expression and organization in humans and animals. The methods of the present invention may be used to produce alterations in a regulatory region for a gene that encodes C/EBPα. Such regulatory sequences can be obtained in a variety of ways. In one preferred method, a gene sequence encoding C/EBPα can be used to probe a genomic library for members that contain the C/EBPα promoter sequence located 5' to the C/EBPα gene. Suitable sequences of the C/EBPα gene are described in FIGS. 1 and 2, and in ATCC Deposit 75412, described in Example 2.

Thus, the invention provides a means for altering the nature or control of transcription or translation of such genes, and of altering such genes. For example, the invention enables one to introduce mutations which result in increased or decreased gene expression. Similarly, it enables one to impair or enhance the transcriptional capacity of the natural allele in order to decrease or increase its expression. Thus, the present invention permits the manipulation and dissection of the C/EBPα gene, and thus permits the identification of C/EBPα variants, antagonists, and synergistic agents.

The molecules and animals of the present invention are particularly suitable for use in the creation and/or study of animal models for disease or tissue degeneration.

The screening assays and animals of the present invention can be used to facilitate the development of novel therapeutic agents that can interact with C/EBPα as well as identify genes that are regulated by C/EBPα.

Thus such assays and animals can evaluate the capacity of a molecule to complement or obviate the loss of C/EBPα expression. Such molecules are functional analogs of C/EBPα. Such analogs include both "classical analogs" and "mimetic analogs." A classical analog of C/EBPα is a molecule that has a similar biological activity, and is chemically related to C/EBPα. By way of illustration, a non-naturally occurring mutant protein having C/EBPα activity would comprise a classical analog of a protein C/EBPα molecule. Similarly, a mutated C/EBPα nucleic acid molecule would comprise an example of a classical analog of a C/EBPα gene sequence. In contrast, a "mimetic analog" of a C/EBPα molecule retains the biological activity of the molecule, but will typically be unrelated chemically. An organic molecule whose structure mimics the active site of a C/EBPα protein would comprise a "mimetic analog" of that protein. Similarly, non-nucleic acid molecules capable of binding to a nucleic acid binding site of C/EBPα, or recognized by C/EBPα would be a mimetic analog of that molecule.

Thus, functional analogs may be either an oligonucleotide or polynucleotide, a proteinaceous compound (including both glycosylated and non-glycosylated proteins), or a non-proteinaceous compound (such as asteroid, a glycolipid, etc.) provided that the agent mimics the function of either an entire C/EBPα nucleic acid molecule, or an oligonucleotide or polynucleotide fragment thereof, or a protein or polypeptide encoded by such a molecule or fragment. Preferred classical analogs include polypeptides (including circular as well as linear peptides) whose sequences comprise the active catalytic or binding sites of an C/EBPα protein, or oligonucleotide fragments of nucleic acid C/EBPα molecules that are capable of either repressing or inducing C/EBPα activity. Preferred mimetic analogs include polypeptides that are not fragments of a C/EBPα protein, or mutants thereof, but nevertheless exhibit a capacity to act in a C/EBPα-like manner, or to induce cellular proliferation in the manner of a C/EBPα antagonist.

Classical analogs can be identified either rationally, as described below, or via established methods of mutagenesis (see, for example, Watson, J. D. et al., *Molecular Biology of the Gene*, Fourth Edition, Benjamin/Cummings, Menlo Park, Calif. (1987). Significantly, a random mutagenesis approach requires no a priori information about the gene sequence that is to be mutated. This approach has the advantage that it assesses the desirability of a particular mutant on the basis of its function, and thus does not require an understanding of how or why the resultant mutant protein has adopted a particular conformation. Indeed, the random mutation of target gene sequences has been one approach used to obtain mutant proteins having desired characteristics (Leatherbarrow, R. J. *Prot. Eng.* 1:7–16 (1986); Knowles, J. R., *Science* 236:1252–1258 (1987); Shaw, W. V., *Biochem. J.* 246:1–17 (1987); Gerit, J. A. *Chem. Rev.* 87:1079–1105 (1987)). Alternatively, where a particular sequence alteration is desired, methods of site-directed mutagenesis can be employed. Thus, such methods may be used to selectively alter only those amino acids of the protein that are believed to be important (Craik, C. S., *Science* 228:291–297 (1985); Cronin, C. S. et al., *Biochem.* 27:4572–4579 (1988); Wilks, H. M. et al., *Science* 242:1541–1544 (1988)). The analysis of such mutants can also be facilitated through the use of a phage display protein ligand screening system (Lowman, H. B. et al., *Biochem.* 30:10832–10838 (1991); Markland, W. et al., *Gene* 109:13–19 (1991); Roberts, B. L. et al., *Proc. Natl. Acad. Sci. (U.S.A.)* 89:2429–2433 (1992); Smith, G. P., *Science* 228:1315–1317 (1985); Smith, R. P. et al., *Science* 248:1126–1128 (1990), all herein incorporated by reference)). In general, this method involves expressing a fusion protein in which the desired protein ligand is fused to the C-terminus of a viral coat protein (such as the M13 Gene III coat protein, or a lambda coat protein).

Mimetic analogs of C/EBPα may be obtained using the principles of conventional or of rational drug design (Andrews, P. R. et al., In: *Proceedings of the Alfred Benzon Symposium*, volume 28, pp. 145–165, Munksgaard, Copenhagen (1990); McPherson, A. *Eur. J. Biochem.* 189:1–24 (1990); Hol, W. G. J. et al., In: *Molecular Recognition: Chemical and Biochemical Problems*, Roberts, S. M. (ed.); Royal Society of Chemistry; pp. 84–93 (1989); Hol, W. G. J., *Arzneim-Forsch*, 39:1016–1018 (1989); Hol, W. G. J., *Agnew. Chem. Int. Ed. Engl.* 25:767–778 (1986) all herein incorporated by reference).

In accordance with the methods of conventional drug design, the desired mimetic molecules are obtained by randomly testing molecules whose structures have an attribute in common with the structure of a "native" C/EBPα molecule, or a molecule that interacts with a C/EBPα molecule. The quantitative contribution that results from a change in a particular group of a binding molecule can be determined by measuring the capacity of competition or cooperativity between the native C/EBPα molecule and the putative mimetic.

In one embodiment of rational drug design, the mimetic is designed to share an attribute of the most stable three-dimensional conformation of a C/EBPα molecule. Thus, the mimetic analog of a C/EBPα molecule may be designed to possess chemical groups that are oriented in a way sufficient to cause ionic, hydrophobic, or van der Waals interactions that are similar to those exhibited by the C/EBPα molecule. In a second method of rational design, the capacity of a C/EBPα to undergo conformational "breathing" is exploited. Such "breathing"—the transient and reversible assumption of a different molecular conformation—is a well appreciated phenomenon, and results from temperature, thermodynamic factors, and from the catalytic activity of the molecule. Knowledge of the 3-dimensional structure of C/EBPα facilitates such an evaluation. An evaluation of the natural conformational changes of a C/EBPα molecule facilitates the recognition of potential hinge sites, potential sites at which hydrogen bonding, ionic bonds or van der Waals bonds might form or might be eliminated due to the breathing of the molecule, etc. Such recognition permits the identification of the additional conformations that C/EBPα could assume, and enables the rational design and production of mimetic analogs that share such conformations.

The preferred method for performing rational mimetic design employs a computer system capable of forming a representation of the three-dimensional structure of C/EBPα (such as those obtained using RIBBON (Priestle, J., *J. Mol. Graphics* 21:572 (1988)), QUANTA (Polygen), InSite (Biosyn), or Nanovision (American Chemical Society). Such analyses are exemplified by Hol, W. G. J. et al. (In: *Molecular Recognition: Chemical and Biochemical Problems*, Roberts, S. M. (ed.); Royal Society of Chemistry; pp. 84–93 (1989)), Hol, W. G. J. (*Arzneim-Forsch.* 39:1016–1018 (1989)), and Hol, W. G. J., *Agnew. Chem. Int. Ed. Engl.* 25:767–778 (1986)).

In lieu of such direct comparative evaluations of putative analogs, screening assays may be used to identify such molecules. Such an assay will preferably exploit the capacity of the analog to affect tumorigenicity. Alternatively, a mutated C/EBPα molecule can be administered with a suspected antagonist compound. The cells would in this case be monitored to determine whether the compound is able to re-establish an inhibition of tumorigenicity.

Such assays are particularly useful for identifying peptide or oligonucleotide fragments of C/EBPα or analogs of such molecules. Thus, for example, one may incubate cells in the presence of either an oligonucleotide or a peptide analog (or fragment) and a suspected antagonist compound. The cells would be monitored in order to determine whether the compound is able to impair the ability of the C/EBPα oligonucleotide to inhibit DNA synthesis. As indicated above, column competition assays could alternatively be conducted. Thus, desired C/EBPα classical and mimetic analogs may be identified by a variety of means.

Having now generally described the invention, the same will be more readily understood through reference to the following examples which are provided by way of illustration, and are not intended to be limiting of the present invention, unless specified.

EXAMPLE 1

Cloning of the C/EBPα Isoform

C/EBPα gene sequences were isolated by screening a λGT10 library made from genomic DNA obtained from the human hepatoma cell line Hep 3B2. The library was probed with rat C/EBPα sequences and a clone containing the entire coding region of human C/EBPα was isolated.

The genomic clone contained approximately 2.2 kb of 5' flanking sequences. An examination of the cloned coding region revealed that the genomic sequence lacked intervening sequences. In lieu of the hepatoma cell line used, any human cell could have been used as the source of the genomic sequences. The coding sequence of the C/EBPα gene is shown in FIG. 1 (SEQ ID NO: 1). The amino acid sequence of C/EBPα is shown in FIG. 2 (SEQ ID NO: 2).

The SEQ ID NO:1 presented herein differs from that described in U.S. patent application Ser. No. 08/029,325 (filed Mar. 4, 1993) in several respects, most notably in including a 65 residue long NotI-NotI oligonucleotide (SEQ ID NO:1 residues 558–622) between residues 556–557 of the prior sequence. The SEQ ID NO:2 presented herein also differs from that described in U.S. patent application Ser. No. 08/029,325 (filed Mar. 4, 1993), most notably in including SEQ ID NO:2 residues 137–156 between residues 134–135 of the prior sequence.

The revised sequences presented herein were obtained from the resequencing of the c/EBPα gene of the c/EBPα vector (ATCC 75412). This vector was deposited with the American Type Culture Collection, Rockville, Md., U.S.A., under the terms of the Budapest Treaty governing microbial deposits. The deposit was made on Feb. 2, 1993, prior to the filing date of U.S. patent application Ser. No. 08/029,325.

EXAMPLE 2

Expression of C/EBPα

The above-isolated C/EBPα coding sequence was expressed using the CMV promoted galactosidase expression vector, CMBβ (MacGregor, G. R. et al., *Nucleic Acids Res.* 17:2365 (1989)). For this purpose, the CMVβ vector was digested with NotI, thereby deleting the β-galactosidase sequences. Human C/EBPα sequences, cloned in plasmid pUC hC/EBPα was digested with NruI and XhoI. A 1.2 kB NruI - XhoI fragment containing the C/EBPα coding sequence plus part of the 5' and 3' untranslated region was isolated by electrophoretic separation through a 1% low melting agarose gel. DNA was recovered from the gel by phenol extraction. The XhoI end of the C/EBPα fragment and the NotI ends of the vector were blunted using the Klenow fragment of DNA polymerase I. The two DNA fragments were then ligated together to form a vector, designated pCMVhC/EBPα, in which C/EBPα is expressed under the control of the CMV promoter (FIG. 3). Vector pCMVhC/EBPα is ampicillin resistant. Vector pCMVhC/EBPα was deposited with the American Type Culture Collection, Rockville, Md., U.S.A., on Feb. 2, 1993, under the terms of the "Budapest Treaty" governing microbial deposits. The deposit was accorded ATCC accession number 75412.

When the above-described vector was transfected into normal proliferating diploid fibroblasts or hepatoma cells an inhibition of cellular growth was observed. C/EBPα was found to have broad inhibitory effects on the proliferation of a number of cell types, including human diploid fibroblasts, human hepatoma cells, HeLa-cervical carcinoma cells, osteosarcoma, and bladder carcinoma, and not just those in which the gene is normally expressed in vivo.

EXAMPLE 3

Growth Inhibitory Capacity of C/EBPα

The above-described expression vector was transfected into a variety of cell lines in order to determine the scope of its growth inhibitory ability.

Expression plasmid was introduced into SAOS-2 (a p53 and rb deficient human osteosarcoma line); 639 (a human T-antigen transformed fibroblast line); TE85 (a human osteosarcome); IEC-6 (a rat gut epithelium cell line); Hep 382 (a human hepatoma line) and MJ (a human diploid fibroblast line). All of these lines, with the exception of MJ and IEC-6 are transformed and were derived from tumors.

The C/EBPα gene was found to be able to inhibit the growth of all cell lines tested, and appeared to have universal inhibitory activity.

EXAMPLE 4

Mapping of Growth Inhibitory Domains of C/EBPα

As indicated above, a salient characteristic of C/EBPα is its ability to inhibit the growth of hepatic and other cell types. In order to determine the regions of the C/EBPα protein that are involved in mediating such growth inhibition, a series of deletions were introduced into the C/EBPα-encoding gene sequence. The mutated sequences were cloned into mammalian vectors and transformed into a human hepatoma line and a human osteosarcoma line.

The expression vectors were prepared by excising the β-galactosidase gene from a CMVβ-gal vector using NotI. The religated vector was designated CMVø. A fragment containing the entire 1.1 kb coding region, 118 base pairs of the 5' leader sequence, and 77 base pairs of 3' untranslated region of the human C/EBPα gene (i.e., from +1 to +1274) was excised from a pUCC/EBPα 3.7 kb vector with NruI and XhoI; this fragment was blunted using the Klenow fragment of DNA polymerase I and cloned into the NotI site of CMVø, which was also blunted, to create CMVα. CMVα30Kd was made by excising an SstII-XhoI fragment (+453 to +1274) from pUCC/EBPα which was blunted and cloned into CMVø. A fragment of the 3.7 kb C/EBPα fragment was excised from pUCC/EBPα using EcoRI and cloned into the EcoRI site of pBluescriptKSII- (Pharmacia); a NotI fragment containing the 3' portion of the gene was excised using the NotI at +585 and the NotI site in the KSII polylinker. This fragment was cloned into the NotI site of CMVø and designated CMVαN/E. CMVα was digested with SmaI to release a fragment from +219 to +478 and a blunt linker (CGGAATTCCG; New England Biolabs, Inc.) (SEQ ID NO:5) was ligated into the SmaI site to restore the correct reading frame; this vector was designated CMVαΔAD1. A fragment of CMVα including the CMV promoter, SV40 splice sites, and 5' portion of C/EBPα to nucleotide +467 was excised with EcoRI-NarI. A second fragment from the NarII site (+893) to the HindIII site in the polylinker, which includes a 3' portion of the gene and the SV40 polyA signal, was also excised from CMVα. These two fragments were ligated into the EcoRI-HindIII sites of pUC19 (BRL, Inc.); this plasmid was identified as CMVαΔAD2. CMVαΔAAD1,2 was created by excising an NaeI fragment (+371 to +853) and inserting a blunt linker (GGAATTCC, New England Biolabs, Inc.) to restore the correct reading frame.

Figure 4:
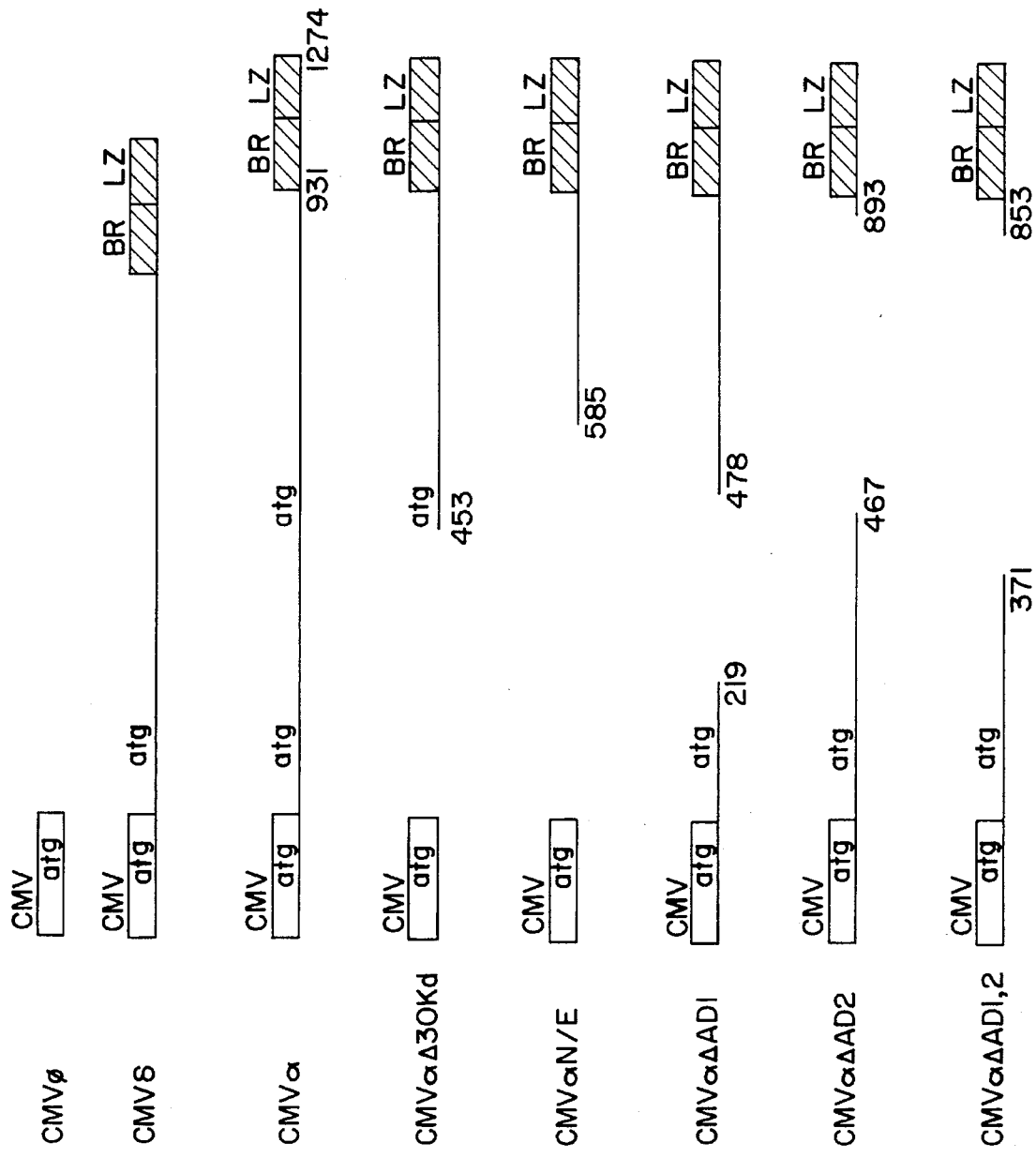
FIG. 4 provides a comparison of the expression vectors used to map the growth inhibitory domains of the C/EBPα gene.

The comparative deletions of the above-described expression vectors is shown in FIG. 4. FIG. 4 also shows the structure of the C/EBPδ gene (designated CMVδ).

Figure 5A:
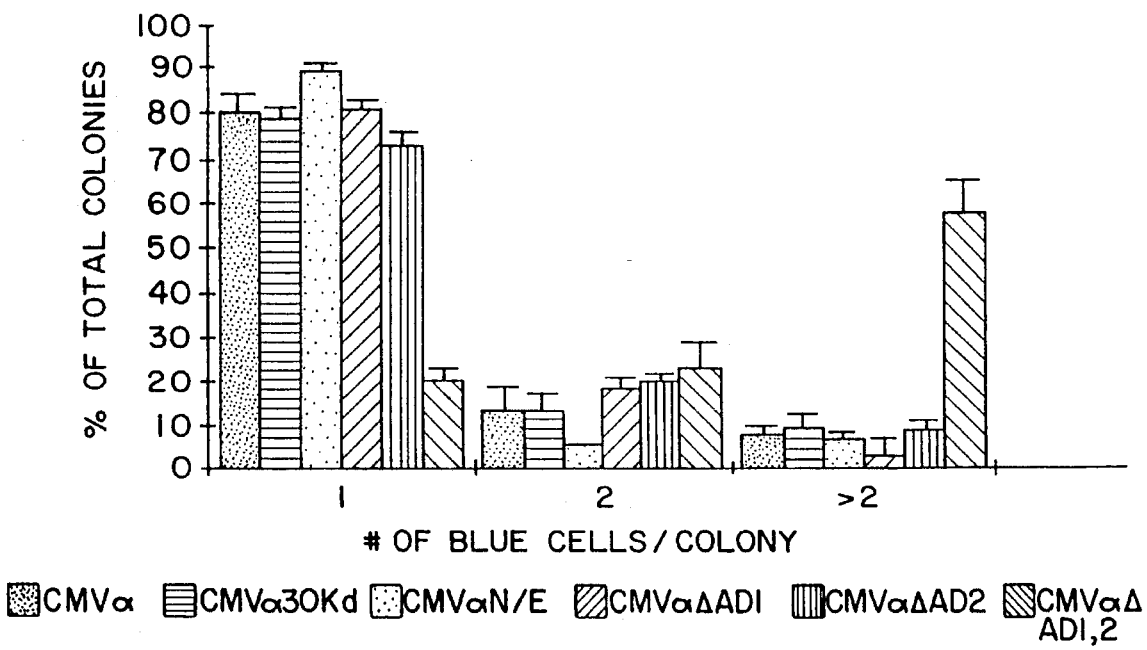
FIGS. 5A and 5B show the growth inhibitory effects of C/EBPα deletion mutants.
Figure 5B:
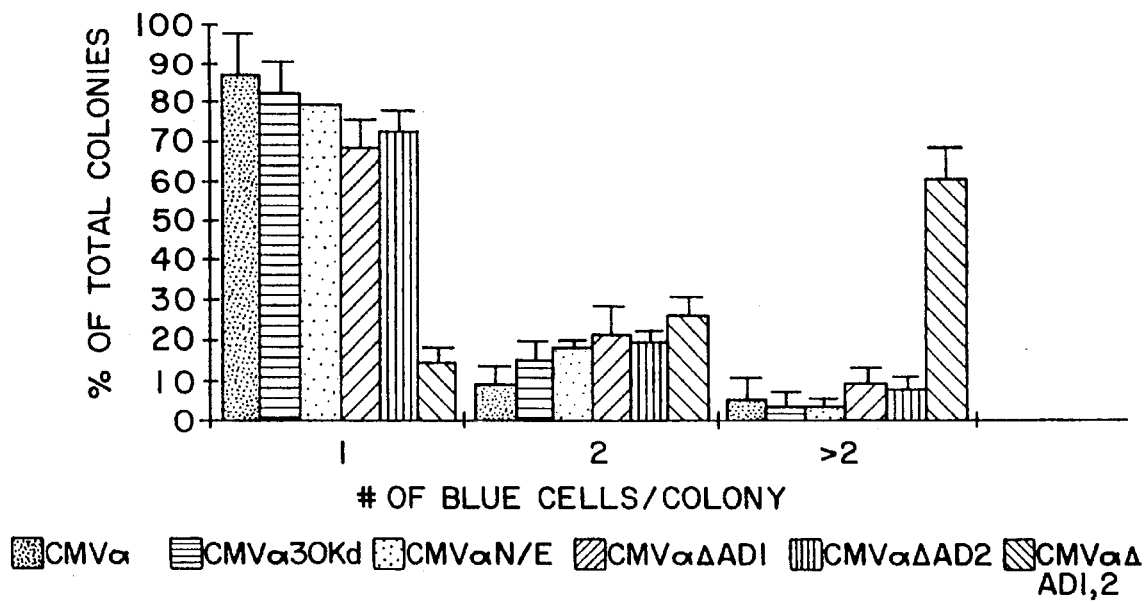

The plasmids were transfected into a human hepatoma cell line (Hep3B2) and into an osteosarcoma cell line (SAOS-2). The osteosarcoma cell line is deficient for both p53 and rb. Cells were cotransfected with one of the above-described C/EBPα deletion mutants and CMVβ-gal at a ratio of 5:1. CMVβ-gal served as the marker of transfected cells. Cells were stained for β-galactosidase activity after 120 hours and the number of blue stained colonies was recorded. Colonies consisted of 1, 2 or more than 2 blue cells, and were categorized accordingly (FIG. 5A, Hep3B2 cells; FIG. 5B, SAOS-2 cells). Colonies of 1 represent cells that did not divide following transfection. In FIGS. 5A and 5B, for each vector, the number of colonies in a category is shown as a percentage of the total number of colonies recorded. Data is presented as the mean ± standard deviations of three separate experiments.

The number of colonies arising after 2 weeks of G418 selection was determined in order to assess the ability of the C/EBPα gene to inhibit cell growth in stably transfected cells. Cells were transfected with 20 μg of a C/EBPα plasmid or a C/EBPα deletion plasmid and 2 μg of a PGKNeo control plasmid. The average number of colonies from two such experiments is shown in Table 1.

TABLE 1

| Plasmid | Number of Colonies Cell Type | |
|---|---|---|
| | Hep3B2 | SAOS-2 |
| CMVø | 76 | 180 |
| CMVβ | 85 | 159 |
| CMVδ | 74 | 210 |
| CMVα | 3 | 5 |
| CMVα30Kd | 13 | 21 |
| CMVαN/E | 9 | 15 |
| CMVαΔAD1 | 12 | 28 |
| CMVαΔAD2 | 20 | 35 |
| CMVαΔAD1,2 | 108 | 140 |

The results indicate that the intact gene, as well as several of the tested deletion mutants, and the C/EBPδ gene were capable of inhibiting the growth of the tumor cells.

The studies of deletion mutants of the human C/EBPα gene further reveal that only a portion of the gene is required for growth inhibition. A deletion construct, CMVαN/E, containing the basic DNA binding regions and the leucine zipper domain as well as 346 base pairs of the transactivation domain was found to be fully active in growth inhibition. CMVαN/E was the smallest construct tested that retained growth inhibitory activity. The growth inhibitory activity of CMVCαN/E indicates that the C/EBP domains that inhibit cellular growth are encoded in a 689 base pair region of the gene.

EXAMPLE 5

Comparative Inhibitory Ability of Human and Rat C/EBPα Genes

In order to assess the relative inhibitory abilities of the human and rat C/EBPα homologs, the above-described CMVC/EBP expression vectors were co-electroporated into cells with CMVβ-gal at a ratio of 5:1. Cells were stained with the substrate x-gal (Sigma Chemical Corp.), which is converted into a blue product by the β-galactosidase enzyme, at time intervals 24, 72, and 120 hours following electroporation. Cell growth was assessed at each time interval by counting the number of blue-stained cells present in each colony or clone of cells that originated from one transfected cell. Transfected cells that had undergone division formed colonies of blue cells, all of which were expected to contain small amounts of the plasmids that had been transfected into the original cell. Cells that did not divide following transfection remained as single blue cells. Colonies containing blue cells were categorized into two groups: clones that remained as single cells, and clones that contained two or more cells.

Figure 6:
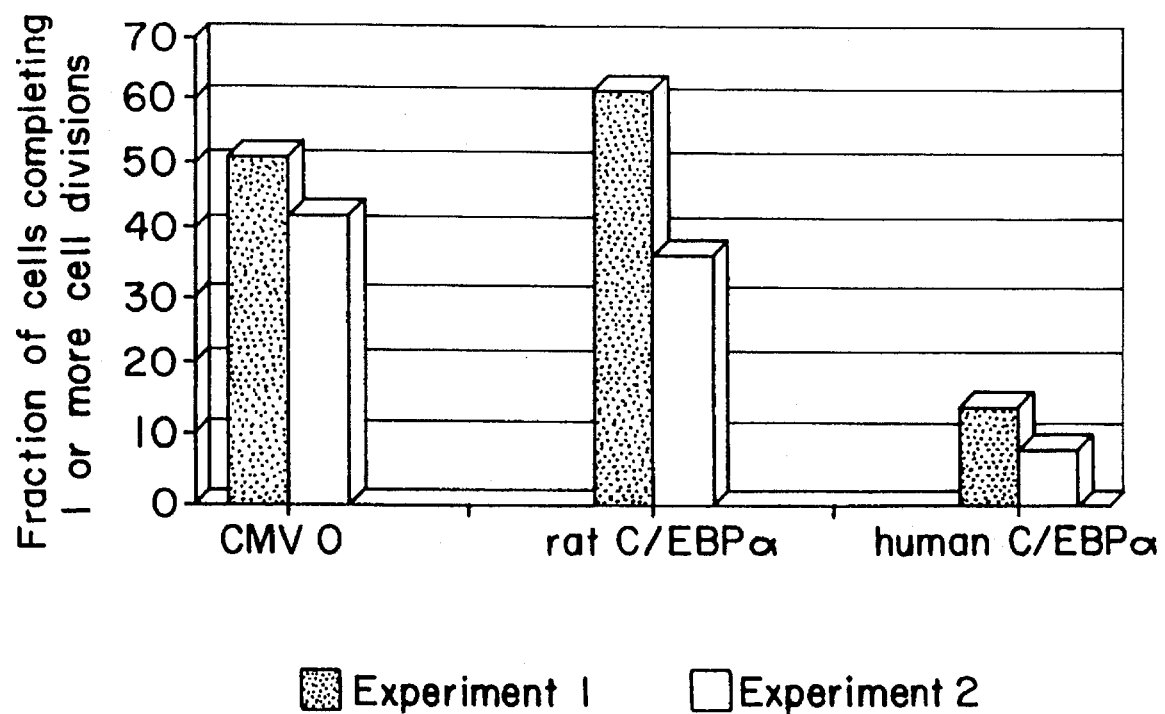
FIG. 6 provides a comparison of the growth inhibitory ability of human and rat C/EBPα.

For each cell line tested, transfection efficiency was determined by staining after 24 hours and calculating the percentage of blue cells present in the total cell population in five microscopic fields. Transient expression of rat or human C/EBPα showed that the rat gene was not inhibitory at day 3 after transfection. At this time, 51% of the control cells (receiving a plasmid that contained no C/EBPα sequences) had undergone at least one division and 61% of the cells receiving rat C/EBPα had divided at least once. In contrast, only 14% of the cells receiving the human C/EBPα gene had completed two divisions. In a second experiment, 42% of the cells receiving the control plasmid had divided at least once by 72 hours. Thirty-six percent of the cells receiving the rat C/EBP gene had undergone division. In contrast, only 8% of cells transfected with human C/EBPα grew. The results are presented in FIG. 6.

EXAMPLE 6

Production of Transgenic Animals that contain Mutations in their Chromosomal C/EBPα Alleles The analysis of the physiological significance of the C/EBP gene was analyzed through the construction of a transgenic mouse that contained a "knock out" mutation in its endogenous chromosomal C/EBPα alleles.

Figure 7:
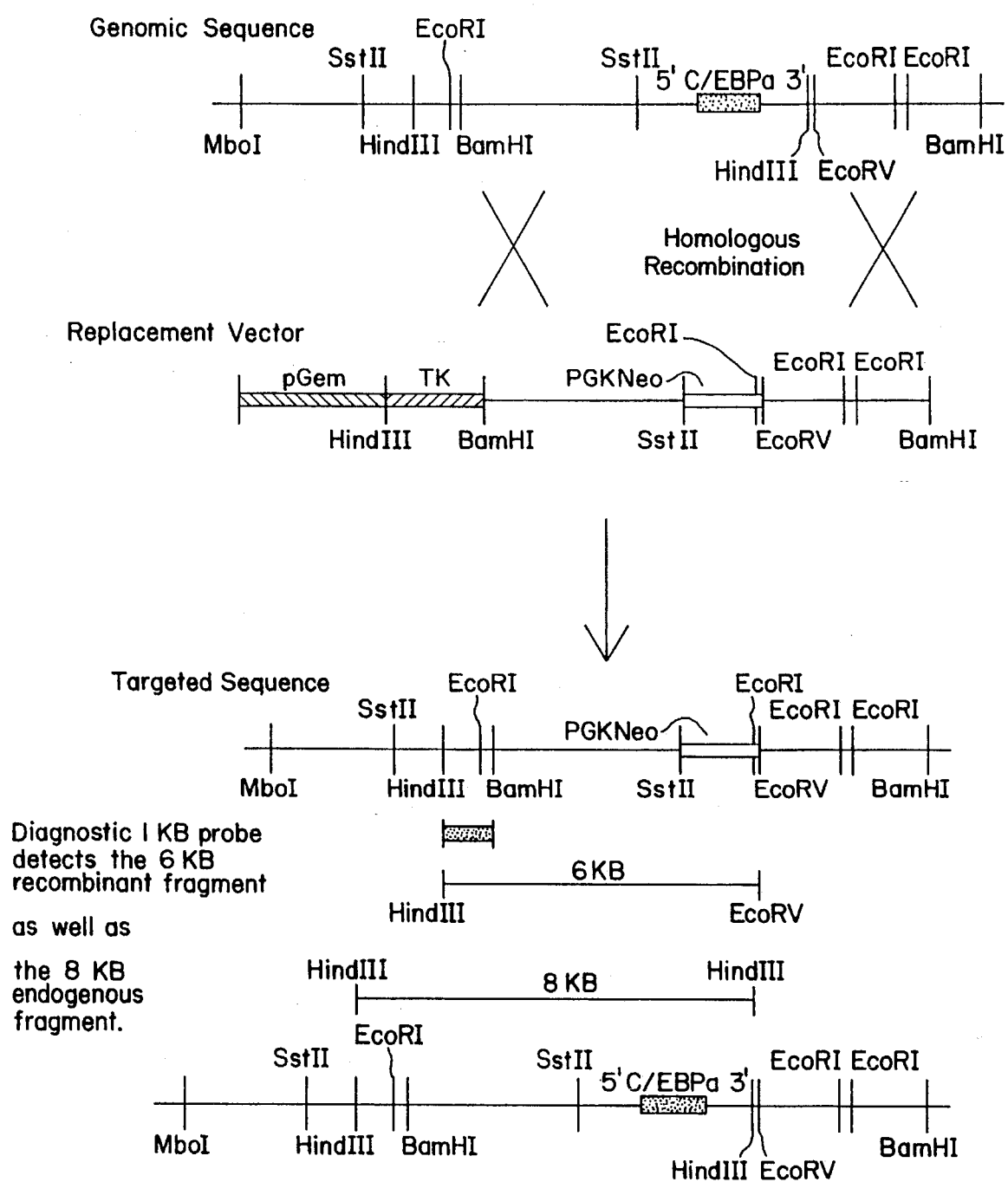
FIG. 7 describes the targeting strategy used to produce transgenic animals that lack endogenous C/EBPα alleles.

A murine SV 129 genomic DNA library was screened for a clone that contained the murine C/EBPα gene and flanking DNA sequences. A 15 kb MboI-HincII fragment was thus isolated and various fragments were subcloned into pBluescript (Pharmacia) vectors. The targeting vectors contained the Herpes simplex thymidine kinase gene, a BamHI-SstI 5' genomic fragment 5' to the C/EBPα gene, the selectable neomycin resistance (NptII) determinant linked to a PGK promoter, and an EcoRV-BamHI genomic fragment 3' to the C/EBPα gene (FIG. 7). The entire C/EBPα gene was replaced by the neomycin resistance determinant. Thus, recombination between the replacement vector and the chromosomal C/EBPα gene accomplishes the deletion of the chromosomal gene sequence.

The vector was linearized at a BamHI site outside of the regions of homology and introduced into murine AB2.1 embryonic stem cells by electroporation. The electroporated cells were subjected to selection for G418 resistance and to sensitivity to gancyclovir. Surviving clones were screened by Southern analysis for evidence of a targeted recombinational event. Such screening was accomplished through the use of a 6 kb HindIII-EcoRV probe that detected the recombinant construct, and through the use of an 8 kb HindIII-HindIII probe of the endogenous genomic sequence (FIG. 7). Three positive clones were identified, and were expanded. The cells were microinjected into developing blastocysts which were then implanted into a foster mother and permitted to develop to term.

Chimeric animals were thus obtained, and were subsequently mated to produce both heterozygous and homozygous C/EBPα deficient "knock-out" mice.

The heterozygous transgenic animals have a substantially normal phenotype. The animals are fertile and grow well. In contrast, the phenotype of the homozygous transgenic animals is a perinatal lethal. The animals have a normal gross anatomy, but die within 6–8 hours of birth. The homozygous animals are hypoglycemic, and injections of glucose will sustain their lives for 30–35 hours. Histologic characterization of the livers of the homozygous animals showed that the animals did not store glycogen in their livers (as do normal mice), nor do they contain fat.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An isolated DNA molecule that encodes human CCAAT/Enhancer Binding Protein C/EBPα.

2. The DNA molecule of claim 1 wherein said molecule comprises the sequence of SEQ ID NO:1.

3. A vector comprising the DNA molecule of claim 1.

4. The vector of claim 3 wherein said human CCAAT/Enhancer Binding Protein C/EBPα is capable of being expressed in a mammalian cell.

5. The vector of claim 4, wherein said mammalian cell is a hepatic cell.

6. An isolated nucleic acid molecule that is complementary to a DNA molecule encoding the human CCAAT/Enhancer Binding Protein C/EBPα.

7. The nucleic acid molecule of claim 6, wherein said molecule is complementary to the sequence of SEQ ID NO:1.

8. The nucleic acid molecule of claim 6 which is detectably labeled.

* * * * *